US012668841B2

(12) United States Patent
Hao et al.

(10) Patent No.: US 12,668,841 B2
(45) Date of Patent: Jun. 30, 2026

(54) IN SITU SEQUENCING OF RNA TRANSCRIPTS WITH NON-UNIFORM 5' ENDS

(71) Applicant: Insitro, Inc., South San Francisco, CA (US)

(72) Inventors: Cynthia Hao, Saratoga, CA (US); Max R. Salick, San Francisco, CA (US); Ci Chu, Palo Alto, CA (US)

(73) Assignee: Insitro, Inc., South San Francisco, CA (US)

( * ) Notice: Subject to any disclaimer, the term of this patent is extended or adjusted under 35 U.S.C. 154(b) by 0 days.

(21) Appl. No.: 18/972,253

(22) Filed: Dec. 6, 2024

(65) Prior Publication Data

US 2025/0101513 A1     Mar. 27, 2025

Related U.S. Application Data

(62) Division of application No. 18/210,970, filed on Jun. 16, 2023, now Pat. No. 12,163,190.

(Continued)

(51) Int. Cl.
*C07H 21/02*          (2006.01)
*C12Q 1/6841*          (2018.01)
(Continued)

(52) U.S. Cl.
CPC ......... *C12Q 1/6874* (2013.01); *C12Q 1/6841* (2013.01); *C12Q 1/6853* (2013.01)

(58) Field of Classification Search
USPC ......... 435/6.1, 6.11, 6.12, 91.1, 91.2, 91.51; 436/94, 501; 536/23.1, 24, 3, 24.33, 25.3
See application file for complete search history.

(56) References Cited

U.S. PATENT DOCUMENTS 11,046,952 B2     6/2021   Blainey et al.
11,214,797 B2     1/2022   Regev et al.
(Continued)

FOREIGN PATENT DOCUMENTS

WO          2019/113499 A1      6/2019
WO          2019/222284 A1      11/2019
(Continued)

OTHER PUBLICATIONS

Lee, J., et al. "Fluorescent in situ sequencing (FISSEQ) of RNA for gene expression profiling in intact cells and tissues", Nature Protocols, 10(3), p. 442 (2015).
(Continued)

*Primary Examiner* — Frank W Lu
(74) *Attorney, Agent, or Firm* — Goodwin Procter, LLP

(57)          ABSTRACT

Disclosed herein are methods for performing in situ sequencing of RNA transcripts with non-uniform 5' ends. During reverse transcription (RT) of RNA transcripts, RT enzyme is induced to "template-switch" to a separate oligonucleotide provided as the template for the upstream flanking region. This flanking region is grafted onto the beginning of the cDNA, enabling padlock probe detection, rolling circle amplification, and fluorescent in situ sequencing. Overall, the disclosed method for in situ sequencing can be applicable for analyzing exogenously introduced transcripts (e.g., identifying and determining impact of a perturbation including a CRISPR perturbation or shRNA/siRNA/ASO perturbation), analyzing naturally occurring transcripts (e.g., measuring gene expression, detecting splicing events), and analyzing modified, naturally occurring transcripts (e.g., detecting mutations or gene edits).

20 Claims, 14 Drawing Sheets

RNA/cDNA
Stage 2

145  5'  140  110A  3'
RNA TSO – Poly-G – – – ——————— 120A

TSO arm
150  sequence – Poly-C – – – ——————— 130
3'  122  5'

135

Related U.S. Application Data

(60) Provisional application No. 63/353,119, filed on Jun. 17, 2022.

(51) Int. Cl.
C12Q 1/6874 (2018.01)
C12Q 1/6853 (2018.01)

(56) References Cited

U.S. PATENT DOCUMENTS

| | | | |
|---|---|---|---|
| 11,345,932 B2 | 5/2022 | Stoner et al. | |
| 11,421,270 B2 | 8/2022 | Feldman et al. | |
| 11,421,273 B2 | 8/2022 | Askary et al. | |
| 11,535,865 B2 | 12/2022 | Feldman et al. | |
| 11,560,561 B2 | 1/2023 | Lim et al. | |
| 2011/0021369 A1 | 1/2011 | Mhlanga et al. | |
| 2014/0315245 A1* | 10/2014 | Yam | C12P 21/00 |
| | | | 435/68.1 |
| 2018/0365372 A1 | 12/2018 | Araya et al. | |
| 2019/0024075 A1 | 1/2019 | Gourguechon et al. | |
| 2019/0161751 A1 | 5/2019 | Kaas et al. | |
| 2019/0203281 A1 | 7/2019 | Robins et al. | |
| 2020/0017852 A1 | 1/2020 | Lee | |
| 2020/0190513 A1* | 6/2020 | Fernandez | C12N 15/113 |
| 2020/0248184 A1 | 8/2020 | Joung et al. | |
| 2020/0283843 A1 | 9/2020 | Regev et al. | |
| 2021/0115436 A1 | 4/2021 | Ramenani et al. | |
| 2021/0163926 A1 | 6/2021 | Labaer et al. | |
| 2021/0164039 A1 | 6/2021 | Wang et al. | |
| 2021/0340527 A1 | 11/2021 | Blainey et al. | |
| 2022/0010367 A1 | 1/2022 | Ramachandran Iyer et al. | |
| 2022/0064633 A1 | 3/2022 | Wei et al. | |
| 2022/0155281 A1 | 5/2022 | Victors et al. | |
| 2022/0229044 A1 | 7/2022 | Feldman et al. | |
| 2022/0325300 A1 | 10/2022 | Stoner et al. | |
| 2022/0396833 A1 | 12/2022 | Askary et al. | |
| 2022/0411850 A1 | 12/2022 | Feldman et al. | |

FOREIGN PATENT DOCUMENTS

| | | | |
|---|---|---|---|
| WO | 2021/091611 A1 | 5/2021 | |
| WO | 2022/178522 A1 | 8/2022 | |

OTHER PUBLICATIONS

Feldman, D., et al., "Lentiviral co-packaging mitigates the effects of intermolecular recombination and multiple integrations in pooled genetic screens", BioRxiv online publication Feb. 8, 2018.

Feldman, D., et al., "Optical Pooled Screens in Human Cells", Cell. Oct. 17, 2019, 179(3), p. 787-799.

Feldman, D., et al., "Pooled genetic perturbation screens with image-based phenotypes", Nature Protocols Feb. 2022; 17(2), p. 476-512.

Dixit, A., et al., "Perturb-Seq: Dissecting Molecular Circuits with Scalable Single-Cell RNA Profiling of Pooled Genetic Screens", Cell. Dec. 15, 2016, 167(7), p. 1853-1866.

Ye, C., et al., "DRUG-seq for miniaturized high-throughput transcriptome profiling in drug discovery", Nature Communications, 9, 4307 (2018).

Radtke, A., et al., "IBEX: an iterative immunolabeling and chemical bleaching method for high-content imaging of diverse tissues", Nature Protocols, 17, pp. 378-401 (Jan. 2022).

Peng, X., et al. "Coupling oligonucleotides possessing a poly-cytosine tag with magnetic ionic liquids for sequence-specific DNA analysis" The Royal Society of Chemistry. 2018; p. 2, 95 second column, last paragraph; Table 1; Retrieved from the Internet: <URL: https://pubs.rsc.org/en/contenVgetauthorversionpdf/c8cc05954c>.

International Search Report and Written Opinion for PCT/US23/ 68577, received Nov. 8, 2023, 28 pages.

Mignardi, M., et al., "Fourth-generation sequencing in the cell and the clinic", Genome Medicine 2014, 6:31.

Picelli, S., et al., "Full-length RNA-seq from single cells using Smart-seq2", Nature Protocols, vol. 9, No. 1, 2014, pp. 171-181.

Ramsköld, D., et al., "Full-Length mRNA-Seq from single cell levels of RNA and individual circulating tumor cells", Nat Biotechnol. Aug. 2012; 30(8): 777-782.

Hagemann-Jensen, et al., "Single-cell RNA counting at allele and isoform resolution using Smart-seq3", Nature Biotechnology, vol. 38, Jun. 2020, pp. 708-714.

Picelli, S., et al., "Smart-seq2 for sensitve full-length transciptome profiling in single cells", Nature Methods, vol. 10, No. 11, Nov. 2013, pp. 1096-1100.

* cited by examiner

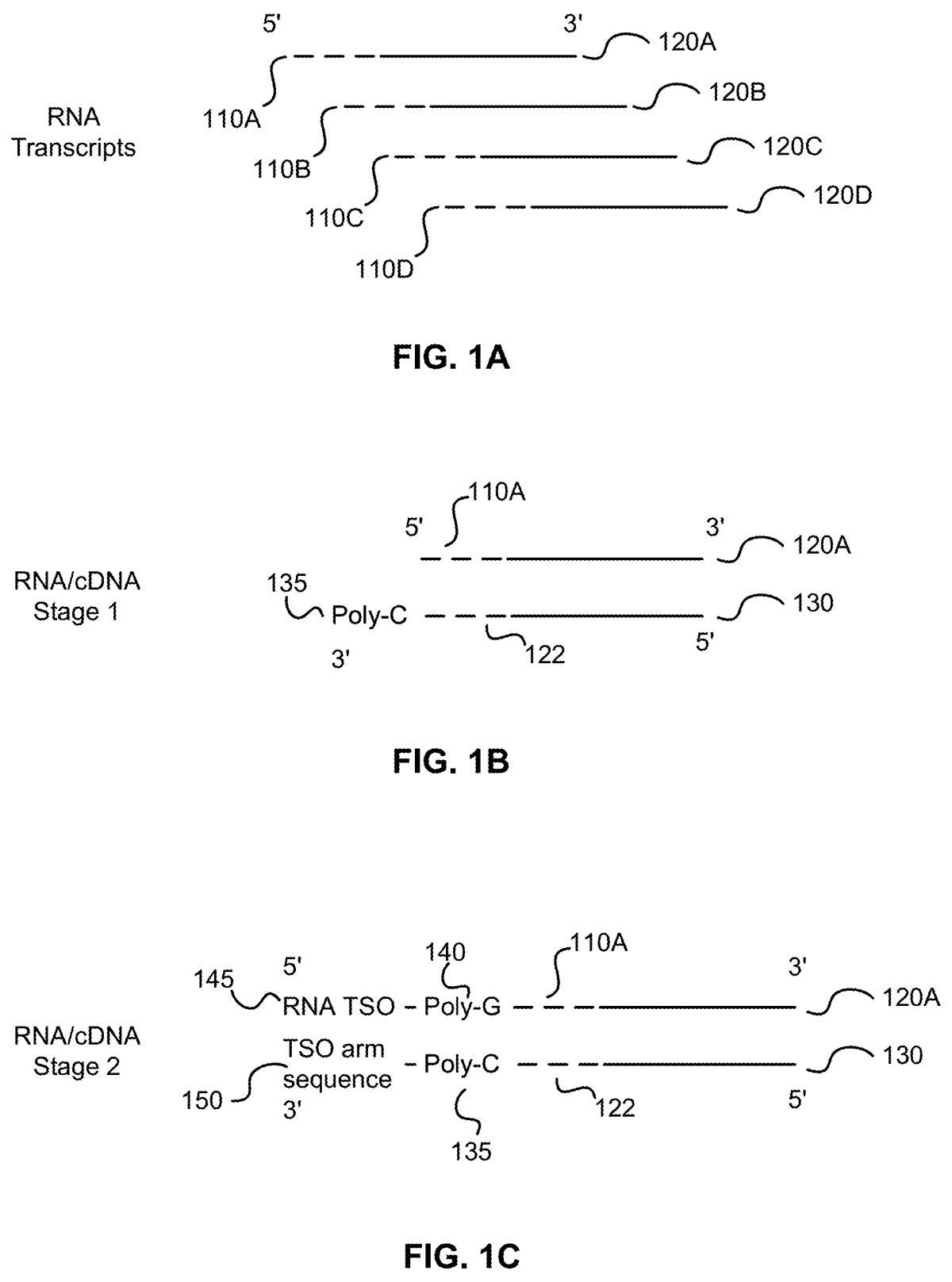

RNA
Transcripts

RNA/cDNA
Stage 1

⌠110A
5'                                    3'
— — ————————— ⌇⟋ 120A
135
⟋Poly-C — — ————————— ⌇⟋ 130
3'              ⌇122              5'

FIG. 1B

RNA/cDNA
Stage 2

145    5'    140    ⌠110A            3'
⟋ RNA TSO – Poly-G — — ——————— ⌇⟋ 120A
TSO arm
sequence – Poly-C — — ————————— ⌇⟋ 130
150 ⌠ 3'              ⌇              5'
                   ⌇122
                   135

FIG. 1C

Circularization

Rolling Circle
Amplification

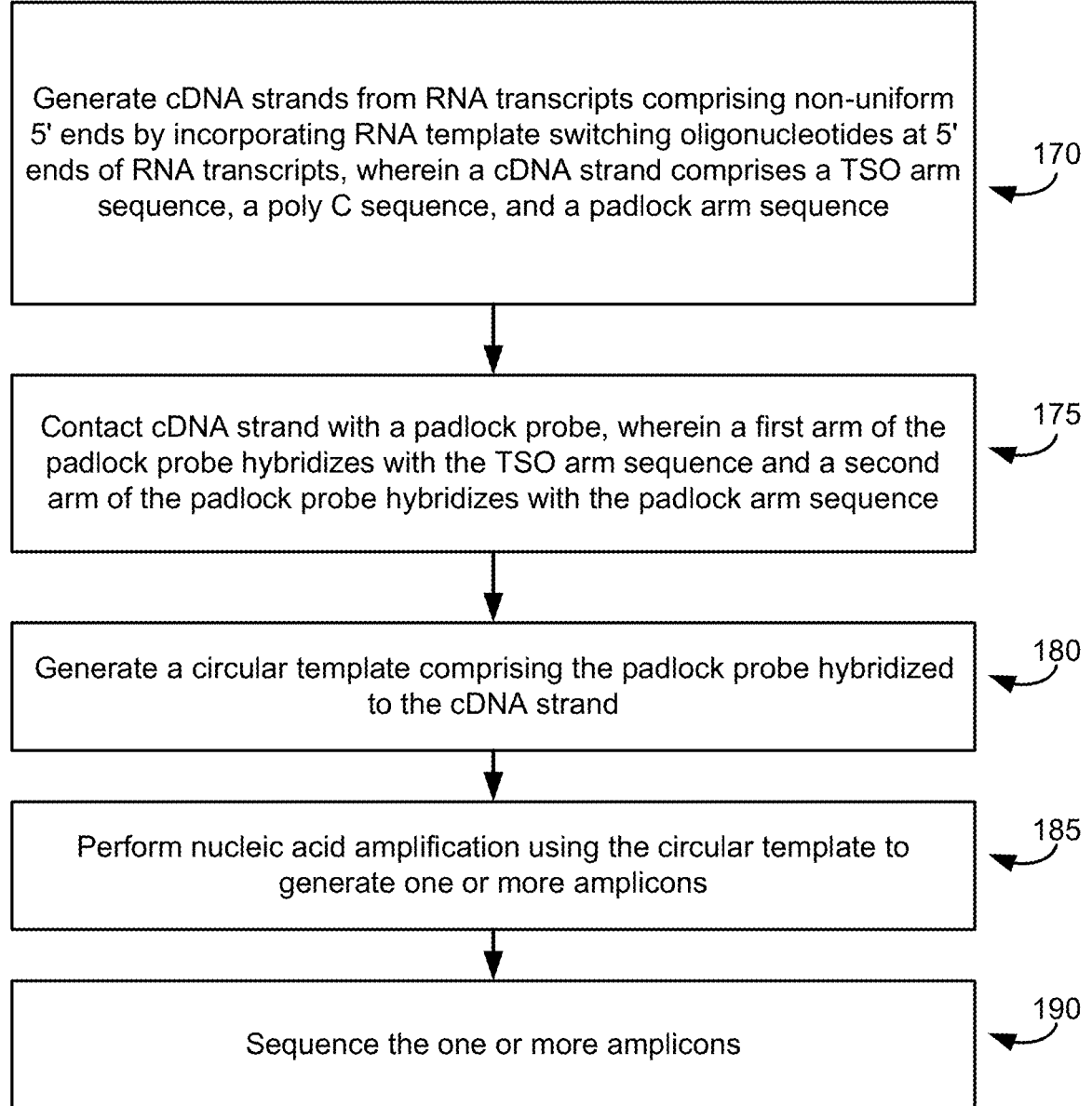

Generate cDNA strands from RNA transcripts comprising non-uniform 5' ends by incorporating RNA template switching oligonucleotides at 5' ends of RNA transcripts, wherein a cDNA strand comprises a TSO arm sequence, a poly C sequence, and a padlock arm sequence          170

Contact cDNA strand with a padlock probe, wherein a first arm of the padlock probe hybridizes with the TSO arm sequence and a second arm of the padlock probe hybridizes with the padlock arm sequence          175

Generate a circular template comprising the padlock probe hybridized to the cDNA strand          180

Perform nucleic acid amplification using the circular template to generate one or more amplicons          185

Sequence the one or more amplicons          190

FIG. 1G pol III guide RNA transcript

Barcode randomly integrated into genomic DNA pol III promoter

5' ———————————————— Barcode   Padlock arm seq   RT priming site ———————————— 3'

5' ———————————————————————————————————— 3'
pol III RNA transcripts
———————————————————————————————————
———————————————————————————————————

Reverse transcription of mRNA starting with barcode

5'   Barcode   Padlock arm seq   RT priming site ———————— RNA 3'

3' C C C — — — — — — — — — —                              cDNA 5'
untemplated 3'C addition
by RT enzyme Template switching to introduce 5′ padlock arm Padlock probe hybridization Barcode gap-filling and ligation Rolling circle amplification (RCA) with phi29 polymerase In situ sequencing of rolling circle amplicon

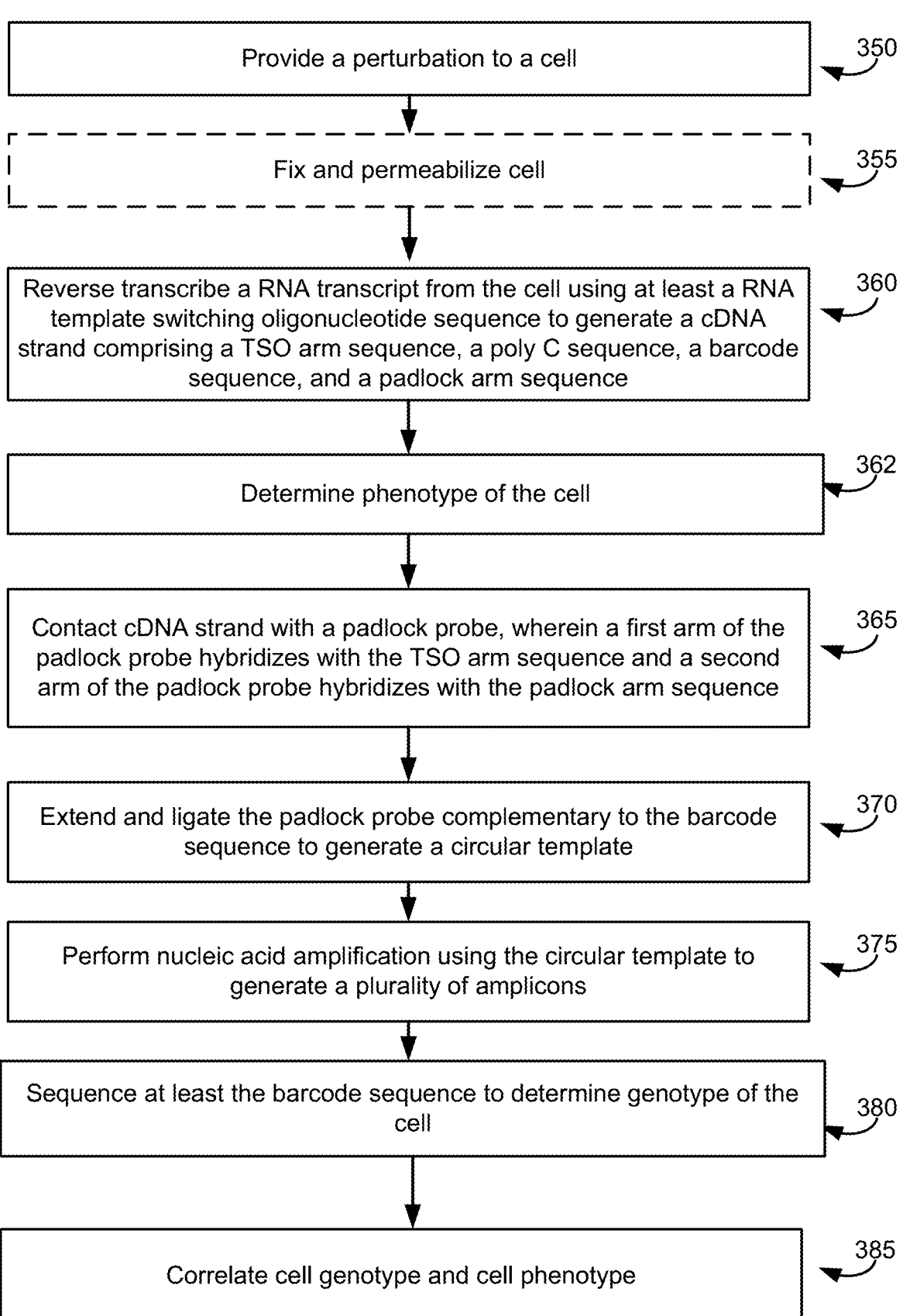

| | |
|---|---|
| Provide a perturbation to a cell | 350 |
| Fix and permeabilize cell | 355 |
| Reverse transcribe a RNA transcript from the cell using at least a RNA template switching oligonucleotide sequence to generate a cDNA strand comprising a TSO arm sequence, a poly C sequence, a barcode sequence, and a padlock arm sequence | 360 |
| Determine phenotype of the cell | 362 |
| Contact cDNA strand with a padlock probe, wherein a first arm of the padlock probe hybridizes with the TSO arm sequence and a second arm of the padlock probe hybridizes with the padlock arm sequence | 365 |
| Extend and ligate the padlock probe complementary to the barcode sequence to generate a circular template | 370 |
| Perform nucleic acid amplification using the circular template to generate a plurality of amplicons | 375 |
| Sequence at least the barcode sequence to determine genotype of the cell | 380 |
| Correlate cell genotype and cell phenotype | 385 |

FIG. 3B

IN SITU SEQUENCING OF RNA TRANSCRIPTS WITH NON-UNIFORM 5' ENDS

CROSS-REFERENCE TO RELATED APPLICATIONS

This application is a divisional of U.S. application Ser. No. 18/210,970, filed Jun. 16, 2023, now granted as U.S. Pat. No. 12,163,190, which claims the benefit of and priority to U.S. Provisional Patent Application No. 63/353,119 filed Jun. 17, 2022, the entire disclosure of which is hereby incorporated by reference in its entirety for all purposes.

BACKGROUND OF THE INVENTION

Understanding cellular organization, development, and disease is dependent on the ability to effectively interrogate cells (e.g., interrogate genes, transcripts, and/or proteins) while keeping the physical structure of the cells intact. In situ sequencing is a promising method for directly sequencing from fixed cells or tissue samples. However, current in situ amplification and sequencing methods require constant regions flanking a variable region of interest. For example, in pooled optical clustered regularly interspaced short palindromic repeats (CRISPR) screening methods, the guide RNAs introduced into cells cannot be directly measured by in situ sequencing, as the polymerase (pol) III-transcribed single guide RNA (sgRNA) would not function properly if a primer binding sequence was introduced prior to the variable region (spacer sequence). One strategy to sidestep this challenge can include inserting the pol III transcript into a larger pol II expression cassette, leveraging the flanking pol II transcript sequence for primer binding and amplification. However this workaround is technically laborious and significantly decreases sequencing signal. Beyond detection of CRISPR sgRNAs, most endogenous RNA transcripts in the cell have only 3' constant regions (poly-A tails) but lack 5' constant regions for amplification, presenting a similar challenge. Due to these limitations, efforts to fully understand cellular organization, development, and disease are constrained by sequencing confidence, cell identification efficiency, and DNA design. For example, a decrease in sequencing signal results in lower sequencing confidence (e.g., lower confidence in barcodes of given cells).

SUMMARY

Disclosed herein are methods for performing in situ sequencing of RNA transcripts with non-uniform 5' ends. Generally, the disclosed methods involve the grafting of a constant region (e.g., through use of template switching oligonucleotides) on cDNA strands which include variable sequences derived from sequences of the non-uniform 5' ends of RNA transcripts. Thus, using the grafted constant region, subsequent steps involve performing template circularization, amplification e.g., rolling circle amplification, and in situ sequencing. As opposed to conventional methods that require constant regions flanking a region of interest, the disclosed methods enable the successful in situ sequencing of variable regions of interest of RNA transcripts that have only a 3' constant region. Thus, in situ sequencing can be performed for RNA transcripts (e.g., RNA transcripts with non-uniform 5' ends) using the methods disclosed herein without the need for constant flanking regions. This enables a broader and more comprehensive understanding of cellular functions and biological pathways.

Specifically, methods disclosed herein involve generating cDNA strands from the RNA transcripts, wherein the generation comprises reverse transcribing the RNA transcripts comprising non-uniform 5' ends, incorporating a RNA template switching oligonucleotide (TSO) at 5' ends of the RNA transcripts, and further performing reverse transcription to incorporate a complement of the RNA TSO sequence in the cDNA. The cDNA strands comprise a template switching oligonucleotide (TSO) arm sequence, a poly C sequence, the variable region (to be sequenced), and a padlock arm sequence. Methods further involve generating a circular template for nucleic acid amplification. For example, methods involve contacting the cDNA strand with a padlock probe, wherein a first arm of the padlock probe hybridizes with the TSO arm sequence and/or the poly C sequence, and wherein a second arm of the padlock probe hybridizes with the padlock arm sequence, and generating a circular template comprising the padlock probe hybridized to the at least one cDNA strand. The circular template is used for performing nucleic acid amplification (e.g., rolling circle amplification). The resulting amplicons are sequenced to obtain the sequences of variable regions of interest, such as sequences of the non-uniform 5' ends of the RNA transcripts.

In particular embodiments, the methods disclosed herein are useful for analyzing exogenous transcripts. For example, an exogenous transcript may include a barcode that is associated with particular information relevant to the transcript. In particular embodiments, methods are useful for sequencing guide RNA (gRNA) libraries in pooled CRISPR screening. Here, the barcode may be associated with, or encode for, a guide RNA that directs a CRISPR protein to provide a perturbation at a particular location in the genomic DNA. Thus, sequencing the barcode sequence is useful for identifying the perturbation that was provided to a cell. In various embodiments, methods are useful for sequencing of shRNA libraries in pooled screening, sequencing of siRNA libraries in pooled screening, sequencing of antisense oligonucleotides (ASOs) introduced into cells, and sequencing of non-perturbing cell labels that differentiate cell lines from others in a pooled setting. In various embodiments, the methods disclosed herein are useful for analyzing naturally occurring transcripts. For example, methods are useful for sequencing RNA transcripts to determine gene expression, sequencing of transcription start sites, and sequencing transcription start sites to detect splicing events. In particular embodiments, the methods disclosed herein are useful for analyzing naturally occurring transcripts that have been modified. For example, methods are useful for sequencing one or more gene edits that are present near a variable 5' RNA end, an example of which can be a transcription start site. As another example, methods are useful for determining the presence or absence of one or more mutations that occur near a variable 5' RNA end, an example of which can be a transcription start site.

Disclosed herein is a method for performing in situ sequencing for a plurality of RNA transcripts comprising non-uniform 5' ends, the method comprising: generating cDNA strands from the plurality of RNA transcripts, wherein the generation comprises reverse transcribing the plurality of RNA transcripts comprising non-uniform 5' ends and incorporating a RNA template switching oligonucleotide (TSO) at 5' ends of one or more RNA transcripts of the plurality, wherein at least one of the cDNA strands comprises: at the 3' end of the cDNA strand, a template switching oligonucleotide (TSO) arm sequence; a poly C sequence;

and a padlock arm sequence; contacting the at least one cDNA strand with a padlock probe, wherein a first arm of the padlock probe hybridizes with the TSO arm sequence and/or the poly C sequence, and wherein a second arm of the padlock probe hybridizes with the padlock arm sequence; generating a circular template comprising the padlock probe hybridized to the at least one cDNA strand; performing nucleic acid amplification using the circular template to generate one or more amplicons; and determining a sequence of the one or more amplicons.

In various embodiments, the plurality of RNA transcripts comprising non-uniform 5' ends comprise, at their respective 5' ends, one or more of: a barcode sequence; a sequence transcribed from a genomic sequence comprising a gene edit; a sequence transcribed from a genomic sequence comprising one or more mutations; and a sequence corresponding to a transcription start site (TSS). In various embodiments, one or more RNA transcripts of the plurality comprise, at their respective 5' ends, a barcode sequence, wherein the barcode sequence encodes for one or more of a guide RNA (gRNA), a small hairpin RNA (shRNA), a small interfering RNA (siRNA), an antisense oligonucleotide, or a non-perturbing cell label. In various embodiments, the barcode sequence is associated with a guide RNA that is specific for a perturbation at a genomic location. In various embodiments, the barcode sequence encodes for a guide RNA that is specific for a perturbation at a genomic location. In various embodiments, the perturbation is a genomic perturbation comprising one or more prime edits or base edits. In various embodiments, the genomic perturbation is imparted by using a CRISPR construct, cDNA construct, a TALEN, or a Zinc finger nuclease. In various embodiments, the perturbation is a transcriptional perturbation. In various embodiments, the transcriptional perturbation is imparted by using a CRISPR interference (CRISPRi) construct or a CRISPR activation (CRISPRa) construct.

In various embodiments, one or more RNA transcripts of the plurality comprise, at their respective 5' ends, a barcode sequence, wherein the barcode sequence is indicative of a non-integrated genomic perturbation. In various embodiments, the non-integrated genomic perturbation modulates expression of a target gene and is encoded by a plasmid. In various embodiments, the barcode sequence is associated with one of a shRNA, a siRNA, or an antisense oligonucleotide that modulates expression of a target gene. In various embodiments, the barcode sequence encodes for one of a shRNA, a siRNA, or an antisense oligonucleotide that modulates expression of a target gene. In various embodiments, methods disclosed herein further comprise determining presence or absence of modulated expression of the target gene using the determined sequence of the one or more amplicons.

In various embodiments, the barcode sequence is randomly inserted into a genome. In various embodiments, the barcode sequence is randomly inserted via a lentiviral construct. In various embodiments, the padlock arm sequence is randomly inserted into the genome along with the barcode sequence. In various embodiments, a reverse transcription primer sequence is inserted into the genome. In various embodiments, the barcode sequence is between 10 and 30 nucleotide bases in length. In various embodiments, generating the circular template comprising the padlock probe hybridized to the at least one cDNA strand comprises extending and ligating a sequence of the padlock probe complementary to the barcode sequence. In various embodiments, determining a sequence of the one or more amplicons comprises determining the barcode sequence of the one or more amplicons.

In various embodiments, methods disclosed herein further comprise determining a cellular genotype based at least in part on the determined barcode sequences of the one or more amplicons. In various embodiments, determining the cellular genotype comprises determining the cellular genotype of a cell in a pooled screening format.

In various embodiments, methods disclosed herein further comprise determining a cellular phenotype of a cell; and correlating the determined cellular genotype with the determined cellular phenotype. In various embodiments, determining the cellular phenotype comprises determining the cellular phenotype in a pooled screening format. In various embodiments, determining the cellular phenotype comprises capturing an image of the cell. In various embodiments, capturing an image of the cell comprises capturing one or more of a fluorescent image, a bright field image, or a phase contrast image. In various embodiments, for the genomic sequence comprising a genetic perturbation, the genomic perturbation comprises one or more prime edits or base edits. In various embodiments, the genomic perturbation is imparted by using a CRISPR construct, cDNA construct, a TALEN, or a Zinc finger nuclease. In various embodiments, for the genomic sequence comprising a genetic perturbation, the genomic perturbation is imparted using a CRISPR interference (CRISPRi) construct or a CRISPR activation (CRISPRa) construct.

In various embodiments, methods disclosed herein further comprise determining a presence or absence of the genetic perturbation using the determined sequence of the one or more amplicons. In various embodiments, for the genomic sequence comprising one or more mutations, the one or more mutations comprise any of a single nucleotide variant (SNV), a single nucleotide polymorphism (SNP), a copy number variation (CNV), an insertion, a deletion, a duplication, an inversion, or a translocation. In various embodiments, methods disclosed herein further comprise determining a presence or absence of the one or more mutations using the determined sequence of the one or more amplicons. In various embodiments, the genomic sequence further comprises a padlock arm sequence. In various embodiments, the padlock arm sequence is a naturally occurring sequence. In various embodiments, the padlock arm sequence is inserted into the genomic sequence. In various embodiments, the padlock arm sequence is inserted into the genomic sequence using a CRISPR construct, cDNA construct, a TALEN, or a Zinc finger nuclease. In various embodiments, the genomic sequence further comprises a reverse transcription primer sequence. In various embodiments, the reverse transcription primer sequence is a naturally occurring sequence in the genomic sequence. In various embodiments, the reverse transcription primer sequence is an inserted genomic sequence. In various embodiments, the inserted reverse transcription primer sequence is inserted into the genomic sequence using a CRISPR construct, cDNA construct, a TALEN, or a Zinc finger nuclease.

In various embodiments, the genomic sequence comprising the genetic perturbation further comprises a transcription start site. In various embodiments, the genomic sequence comprising the genetic perturbation is located within 100 nucleotide bases downstream of a transcription start site. In various embodiments, the sequence corresponding to the TSS comprises a sequence transcribed from a genomic sequence comprising the TSS. In various embodiments, the sequence corresponding to the TSS comprises a sequence transcribed from a genomic sequence located within 100 nucleotide bases downstream of a TSS.

In various embodiments, methods disclosed herein further comprise determining expression levels of a RNA transcript comprising the TSS sequence using the determined sequence of the one or more amplicons. In various embodiments, methods disclosed herein further comprise mapping the sequence at the 5' end of a RNA transcript to a TSS using the determined sequence of the one or more amplicons. In various embodiments, methods disclosed herein further comprise determining a presence, absence, or expression levels of the TSS using the determined target sequence of the one or more amplicons. In various embodiments, the sequence corresponding to the TSS comprises a RNA transcript comprising a sequence generated from a splicing event. In various embodiments, the splicing event is one or more of a splice variant, a fusion, an intra-genic rearrangement, a deletion, an insertion, a novel/extended exon, a novel exon junction substitution, or a retained intron. In various embodiments, methods disclosed herein further comprise determining a presence, absence, or expression levels of the splicing event using the determined sequence of the one or more amplicons. In various embodiments, the sequence corresponding to the TSS comprises a sequence at a start of a RNA fragment. In various embodiments, the sequence at the start of the RNA fragment is transcribed along with the TSS.

In various embodiments, reverse transcribing the plurality of RNA transcripts and incorporating the RNA TSO comprises: generating a cDNA strand complementary to one of the plurality of RNA transcripts using a reverse transcriptase, the cDNA strand comprising an untemplated poly C sequence, hybridizing an poly G sequence to the poly C sequence, wherein the RNA TSO comprises the poly G sequence; and further extending the cDNA strand to incorporate the TSO arm sequence complementary to the RNA TSO. In various embodiments, the plurality of RNA transcripts are transcribed from a single cell and comprise diverse sequences. In various embodiments, the plurality of RNA transcripts are transcribed from a plurality of cells and comprise diverse sequences. In various embodiments, the sequence of the one or more amplicons is determined using a sequencing by synthesis method.

In various embodiments, the sequence of the one or more amplicons is determined optically. In various embodiments, the sequence of the one or more amplicons is determined using fluorescence in situ hybridization. In various embodiments, the sequence of the one or more amplicons is determined using fluorescent in situ sequencing (FISSEQ). In various embodiments, generating the circular template comprising the padlock probe hybridized to the at least one cDNA strand comprises extending the second arm of the padlock probe and ligating the extended second arm to a poly G sequence of the padlock probe. In various embodiments, the poly G sequence comprises between 2 to 5 guanine nucleobases. In various embodiments, the poly C sequence comprises between 2 to 5 cytosine nucleobases. In various embodiments, the reverse transcriptase is Moloney murine leukemia (M-MLV) RT enzyme.

In various embodiments, contacting the at least one cDNA strand with a padlock probe further comprises digesting the plurality of RNA transcripts. In various embodiments, digesting the plurality of RNA transcripts comprises contacting the RNA transcripts with RNAse H. In various embodiments, performing nucleic acid amplification using the circular template further comprises using an amplification primer and a polymerase to extend around the circular template. In various embodiments, the amplification primer is generated by digesting a portion of the TSO arm sequence using an exonuclease. In various embodiments, the exonuclease is a phi29 polymerase. In various embodiments, determining a sequence of the one or more amplicons comprises sequencing the one or more amplicons. In various embodiments, sequencing the one or more amplicons comprises: incorporating a plurality of reversibly terminated nucleobases comprising tags into the one or more amplicons; determining a presence of the incorporated reversibly terminated nucleobases; and cleaving the base terminators and the tags.

In various embodiments, methods disclosed herein further comprise prior to reverse transcribing the plurality of RNA transcripts, fixing and permeabilizing one or more cells comprising the plurality of RNA transcripts. In various embodiments, the RNA TSO comprises one or more locked nucleic acids (LNA). In various embodiments, the RNA TSO comprises one LNA at a 3' end of the RNA TSO. In various embodiments, between 1% and 50% of the nucleotides of the RNA TSO comprise locked nucleic acids.

In various embodiments, the plurality of RNA transcripts are derived from one or more cells, wherein the one or more cells are induced pluripotent stem cells (iPSC), cancer cells, primary cells, or differentiated cells. In various embodiments, at least one of the one or more cells exhibit pol II transcript silencing. In various embodiments, at least one of the plurality of RNA transcripts is transcribed from a genomic sequence located less than 100, less than 50, less than 25, less than 20, less than 15, less than 10, or less than 5 nucleobases downstream of a pol II or pol III promoter. In various embodiments, transcription of at least one of the plurality of RNA transcripts is controlled by a pol III promoter, and wherein transcription of at least another one of the plurality of RNA transcripts is controlled by a pol II promoter.

Additionally disclosed is a construct for performing rolling circle amplification, the construct comprising: a RNA transcript; and a cDNA strand hybridized with the RNA transcript, wherein the cDNA strand comprises: a template switching oligonucleotide (TSO) arm sequence; an poly C sequence; and a padlock arm sequence; and a RNA template switching oligonucleotide (TSO) comprising a poly G sequence, wherein the poly G sequence is hybridized to the poly C sequence of the cDNA strand, and wherein a portion of the RNA TSO is hybridized to the TSO arm sequence of the cDNA strand. In various embodiments, the cDNA strand further comprises a barcode sequence associated with one of a guide RNA (gRNA), a small hairpin RNA (shRNA), a small interfering RNA (siRNA), an antisense oligonucleotide, or a non-perturbing cell label. In various embodiments, the cDNA strand further comprises a barcode sequence encoding for one of a guide RNA (gRNA), a small hairpin RNA (shRNA), a small interfering RNA (siRNA), an antisense oligonucleotide, or a non-perturbing cell label. In various embodiments, the poly C sequence comprises between 2 to 5 cytosine nucleobases. In various embodiments, the poly G sequence comprises between 2 to 5 guanine nucleobases.

In various embodiments, the RNA TSO comprises one or more locked nucleic acids (LNAs). In various embodiments, the RNA TSO comprises one LNA at a 3' end of the RNA TSO. In various embodiments, between 1% and 50% of the nucleotides of the RNA template switching oligonucleotide comprise locked nucleic acids. In various embodiments, the RNA transcript further comprises a reverse transcription priming site. In various embodiments, the cDNA strand further comprises a sequence complementary to the reverse transcription priming site. In various embodiments, the RNA transcript is a pol III-transcribed RNA transcript. In various embodiments, the RNA transcript further comprises a target sequence, and wherein the cDNA strand further comprises a reverse complement of the target sequence.

Additionally disclosed herein is a construct for performing rolling circle amplification, the construct comprising: a cDNA strand reverse transcribed from a RNA transcript, wherein the cDNA strand comprises: a template switching oligonucleotide (TSO) arm sequence; an poly C sequence; a padlock arm sequence; a padlock probe, wherein a first arm of the padlock probe is hybridized with the TSO arm sequence and the poly C sequence, and wherein a second arm of the padlock probe hybridizes with the padlock arm sequence. In various embodiments, the cDNA strand further comprises a barcode sequence associated with one of a guide RNA (gRNA), a small hairpin RNA (shRNA), a small interfering RNA (siRNA), an antisense oligonucleotide, or a non-perturbing cell label. In various embodiments, the cDNA strand further comprises a barcode sequence encoding for one of a guide RNA (gRNA), a small hairpin RNA (shRNA), a small interfering RNA (siRNA), an antisense oligonucleotide, or a non-perturbing cell label. In various embodiments, the poly C sequence comprises between 2 to 5 cytosine nucleobases. In various embodiments, the cDNA strand further comprises a sequence complementary to a reverse transcription priming site of the RNA transcript. In various embodiments, the RNA transcript is a pol III-transcribed RNA transcript. In various embodiments, the RNA transcript further comprises a target sequence, and wherein the cDNA strand further comprises a reverse complement of the target sequence.

BRIEF DESCRIPTION OF THE DRAWINGS

These and other features, aspects, and advantages of the present invention will become better understood with regard to the following description and accompanying drawings. It is noted that wherever practicable similar or like reference numbers may be used in the figures and may indicate similar or like functionality. For example, a letter after a reference numeral, such as "RNA transcript 120A," indicates that the text refers specifically to the element having that particular reference numeral. A reference numeral in the text without a following letter, such as "RNA transcript 120," refers to any or all of the elements in the figures bearing that reference numeral (e.g. "RNA transcript 120" in the text refers to reference numerals "RNA transcript 120A," "RNA transcript 120B," "RNA transcript 120C," and/or "RNA transcript 120D" in the figures).

FIGS. 1A-1F show an overall schematic for performing in situ sequencing of RNA transcripts with non-uniform 5' ends, in accordance with an embodiment.

FIG. 1G shows a flow diagram for performing in situ sequencing of RNA transcripts with non-uniform 5' ends, in accordance with an embodiment.

8

FIG. 3B depicts a flow process for determining cellular genotypes and phenotypes, in accordance with an embodiment.

Figure 4A:
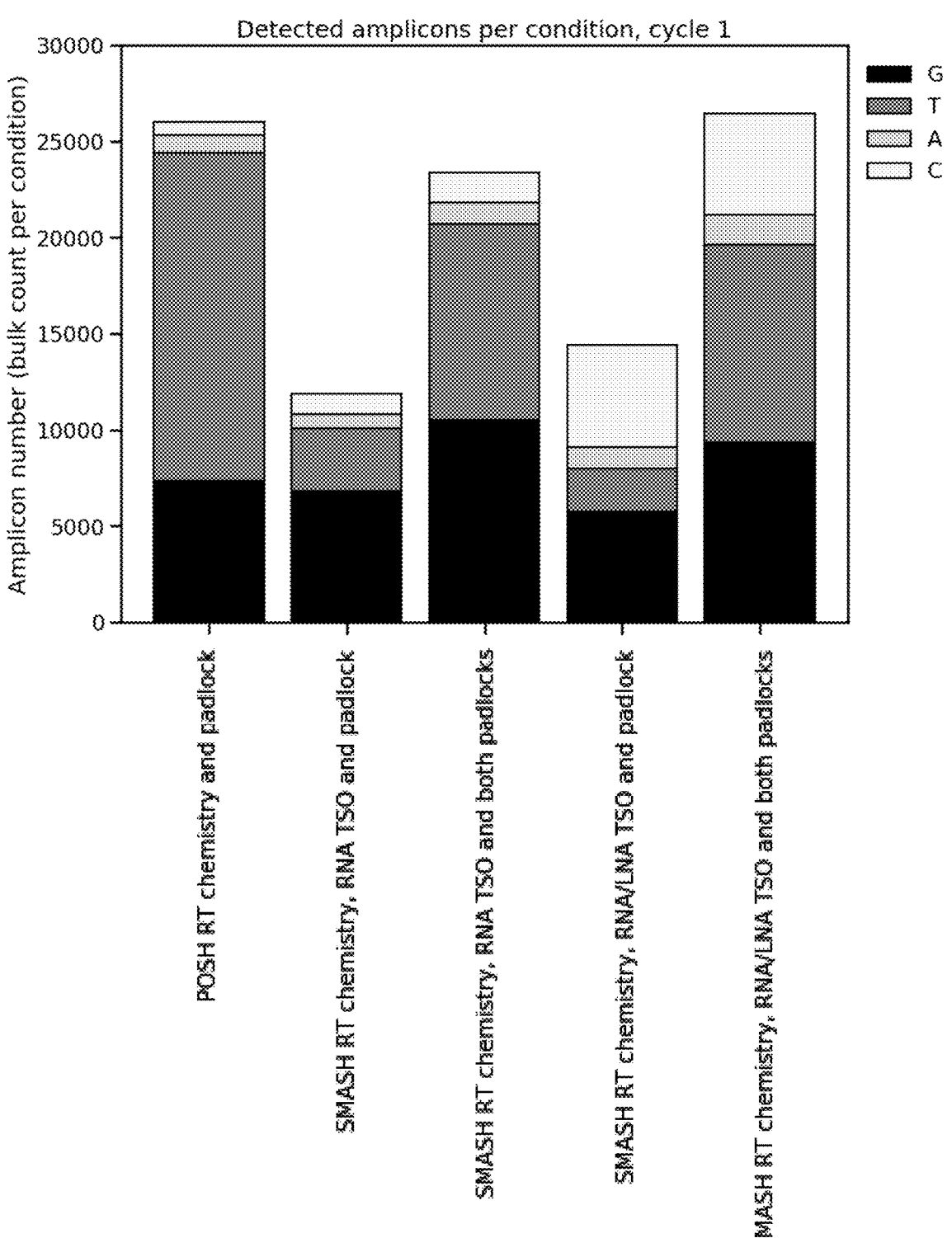
Figure 4B:
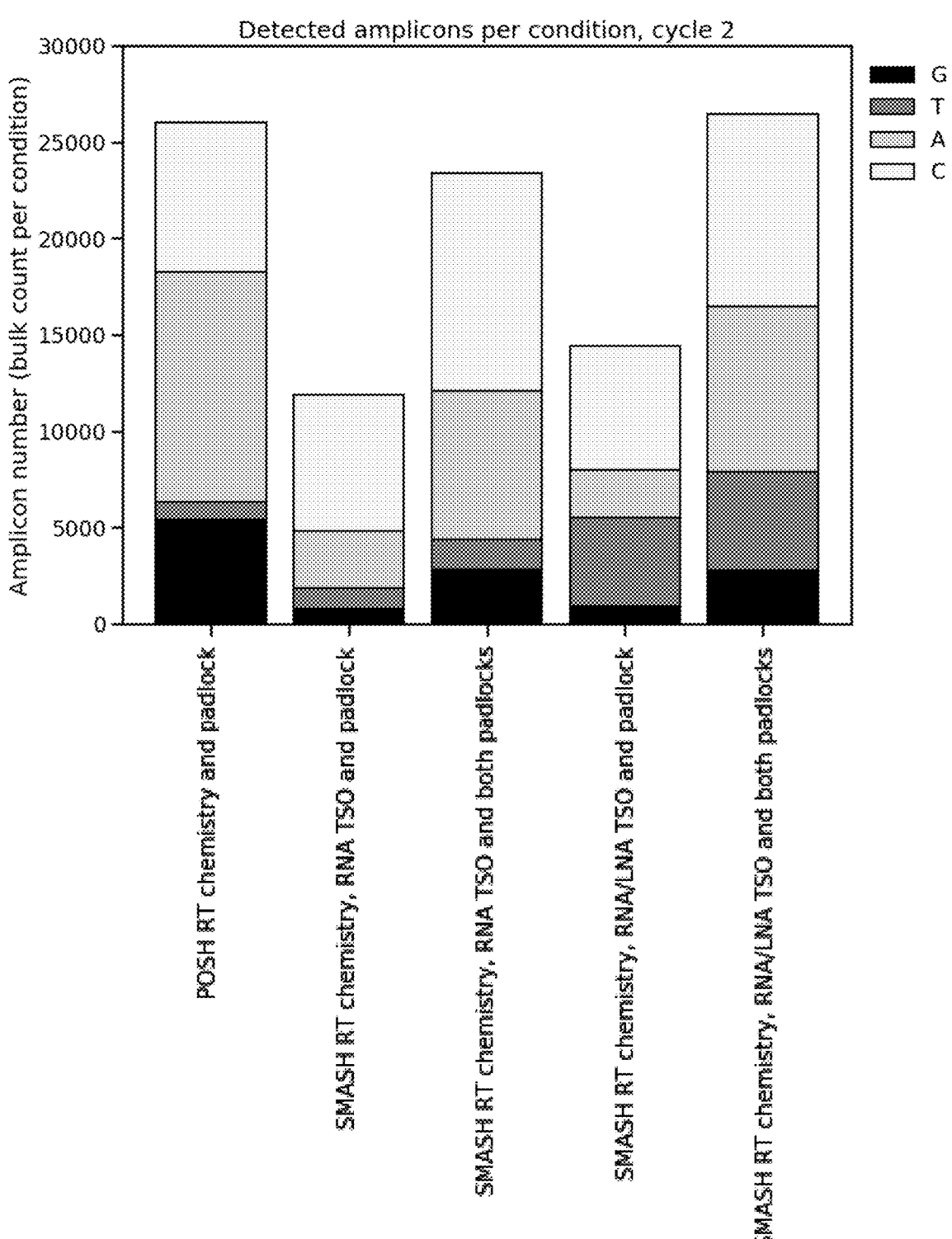

FIGS. 4A and 4B show quantities of detected amplicons using various embodiments of the disclosed methodology.

Figure 5:
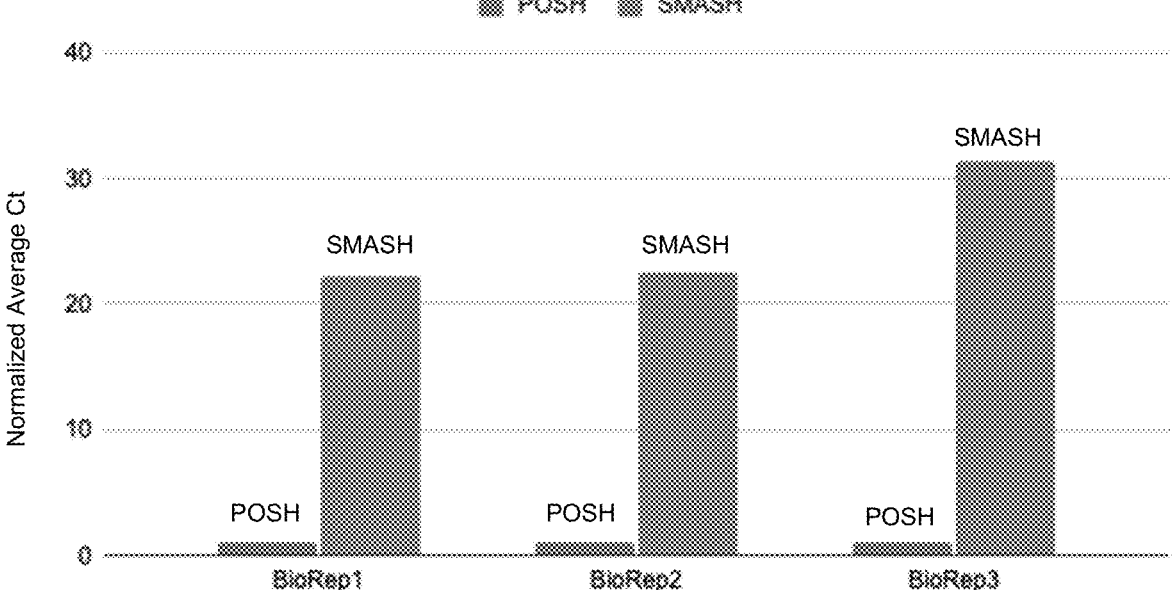

FIG. 5 depicts the normalized Ct values for pooled optical screening in humans (POSH) and SMASH over the three technical replicates.

DETAILED DESCRIPTION OF THE INVENTION

Definitions

Terms used in the claims and specification are defined as set forth below unless otherwise specified.

The phrase "RNA transcripts comprising non-uniform 5' ends" refers to RNA transcripts with variable regions located at their 5' ends. In particular embodiments, one or more RNA transcripts have sequences at their 5' ends that differ from sequences at 5' ends of one or more additional RNA transcripts. In various embodiments, the non-uniform 5' end of a RNA transcript comprises any of a barcode sequence, a sequence transcribed from a genomic sequence comprising a gene edit, a sequence transcribed from a genomic sequence comprising one or more mutations; and a sequence corresponding to a transcription start site (TSS).

The phrases "RNA template switching oligonucleotide" or "RNA TSO" refer to a RNA-based template switching oligonucleotide molecule. In various embodiments, the RNA TSO includes one or more ribonucleotides. In various embodiments, the RNA TSO includes one or more locked nucleic acids (LNAs). In particular embodiments, the RNA TSO includes a poly G sequence that enables the template switching.

The phrase "a template switching oligonucleotide (TSO) arm sequence" refers to a sequence of a cDNA strand. Generally, the TSO arm sequence of the cDNA strand represents a constant region that is incorporated onto an end of the cDNA strand which enables subsequent template circularization, rolling circle amplification, and sequencing. In various embodiments, the TSO arm sequence is complementary to a sequence of a template switching oligonucleotide (TSO), such as a RNA TSO. In various embodiments, the TSO arm sequence of the cDNA strand is generated through reverse transcription.

The phrase "poly C sequence" refers to a cytosine homopolymer sequence. In various embodiments, the poly C sequence comprises between 2 to 9 cytosine nucleobases, between 2 to 8 cytosine nucleobases, between 2 to 7 cytosine nucleobases, between 2 to 6 cytosine nucleobases, between 2 to 5 cytosine nucleobases, or between 2 to 4 cytosine nucleobases. In particular embodiments, the poly C sequence comprises between 2 to 5 cytosine nucleobases. In various embodiments, the poly C sequence is generated on a cDNA strand by reverse transcriptase. The poly C sequence enables template switching using a RNA template switching oligonucleotide.

The phrase "poly G sequence" refers to a guanine homopolymer sequence. In various embodiments, the poly G sequence comprises between 2 to 9 guanine nucleobases, between 2 to 8 guanine nucleobases, between 2 to 7 guanine nucleobases, between 2 to 6 guanine nucleobases, between 2 to 5 guanine nucleobases, or between 2 to 4 guanine nucleobases. In particular embodiments, the poly G sequence comprises between 2 to 5 cytosine nucleobases. In various embodiments, the poly G sequence is included as part of a RNA TSO molecule. Thus, the poly G sequence can hybridize with a corresponding poly C sequence of a cDNA strand, thereby enabling template switching.

The phrase "padlock arm sequence" refers to a sequence of a cDNA strand that hybridizes with a corresponding sequence of an arm of a padlock probe. In various embodiments, the padlock arm sequence is a constant region such that multiple cDNA strands each have the same padlock arm sequence. Thus, copies of the same padlock probe can hybridize with the same padlock arm sequence of the multiple cDNA strands. In various embodiments, the padlock arm sequence in cDNA strands derives from a naturally occurring sequence in the genome. In various embodiments, the padlock arm sequence in cDNA strands derives from a constant sequence that is inserted into the genome (e.g., inserted via gene editing methods).

The phrase "incorporating a RNA template switching oligonucleotide (TSO) at a 5' end of a RNA transcript" generally encompasses the use of a RNA TSO at the 5' end of a RNA transcript to template switch between a cDNA strand and the RNA transcript. In various embodiments, incorporating a RNA TSO does not involve directly linking the RNA TSO to the 5' end of the RNA transcript. For example, following reverse transcription, an untemplated poly-C sequence is added at a 3' end of a cDNA strand. Incorporating a RNA TSO involves hybridizing a poly-G sequence to the poly-C sequence, where the RNA TSO is linked to the poly-G sequence (which is not directly linked to the 5' end of the RNA transcript). Thus, this enables template switching such that the RNA TSO sequence can serve as the template for additional reverse transcription to further generate a complementary sequence (e.g., a TSO arm sequence) in the cDNA strand.

Primers and oligonucleotides used in embodiments herein comprise nucleotides. A nucleotide comprises any compound, including without limitation any naturally occurring nucleotide or analog thereof, which can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. For example, the nucleotide can optionally include a chain of phosphorus atoms comprising two, three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, BH3, or S. In the phosphorus chain, a phosphorus atom with a side group other than O can be a substituted phosphate group. In the phosphorus chain, phosphorus atoms with an intervening atom other than O can be a substituted phosphate group.

In some embodiments, the nucleotide comprises a label and referred to herein as a "labeled nucleotide"; the label of the labeled nucleotide is referred to herein as a "nucleotide label." In some embodiments, the label can be in the form of a fluorescent moiety (e.g. dye), luminescent moiety, or the like attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, locked nucleic acids (LNAs) peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

It must be noted that, as used in the specification and the appended claims, the singular forms "a," "an" and "the" include plural referents unless the context clearly dictates otherwise.

Overview

Disclosed herein are methods for performing in situ sequencing of RNA transcripts with non-uniform 5' ends. Generally, methods enable the capturing, amplification, and sequencing of any region of interest at the beginning (e.g., 5' end) of a RNA transcript. By removing the requirement for an upstream constant flanking region, RNA transcripts with non-uniform 5' ends can be sequenced. As disclosed herein, during reverse transcription (RT) of RNA transcripts, the RT enzyme is induced to "template-switch" to a separate oligonucleotide provided as the template for the upstream flanking region. This flanking region is grafted onto the beginning of the cDNA, enabling padlock probe detection and rolling circle amplification. Overall, the disclosed method for in situ sequencing can achieve higher efficiency at detecting transcripts, is more resistant to silencing, and is more robust to sequencing error for any given cell.

Specifically, the methods involve incorporating template switching oligonucleotides (TSOs) at 5' ends of the RNA transcripts. This enables incorporation of a corresponding complementary TSO arm sequence in the cDNA strand. Here, the corresponding complementary TSO arm sequence is a constant sequence that resides at the 3' end of the cDNA strand. Circular templates are generated using the TSO arm sequences of the cDNA strands, followed by nucleic acid amplification, and sequencing (e.g., in situ sequencing).

Reference is now made to FIGS. 1A-IE, which show an overall schematic for performing in situ sequencing of RNA transcripts with non-uniform 5' ends, in accordance with an embodiment. FIG. 1A depicts a plurality of RNA transcripts 120A, 120B, 120C, and 120D. Here, the RNA transcripts 120 may include non-uniform 5' ends. For example, RNA transcript 120A includes a non-uniform 5' end 110A, RNA transcript 120B includes a non-uniform 5' end 110B, RNA transcript 120C includes a non-uniform 5' end 110C, and RNA transcript 120D includes a non-uniform 5' end 110D. Although FIG. 1A shows four different RNA transcripts 120, in various embodiments, methods for performing in situ sequencing involve additional RNA transcripts, such as at least 5 RNA transcripts, at least 10 RNA transcripts, at least 25 RNA transcripts, at least 50 RNA transcripts, at least 100 RNA transcripts, at least 500 RNA transcripts, at least 1000 RNA transcripts, at least 5000 RNA transcripts, at least 10,000 RNA transcripts, at least 50,000 RNA transcripts, at least 100,000 RNA transcripts, at least 500,000 RNA transcripts, at least 1,000,000 RNA transcripts, at least 5,000,000 RNA transcripts, at least 10,000,000 RNA transcripts, or at least 50,000,000 RNA transcripts.

In various embodiments, the RNA transcripts 120 may originate from a single cell. In various embodiments, the RNA transcripts 120 originate from different cells. The RNA transcripts 120 originating from a single cell or the RNA transcripts 120 originating from different cells may comprise diverse sequences (e.g., sequences from RNA transcripts are different from one another). Further details of cells are described herein.

In various embodiments, RNA transcripts 120 are transcribed from different genomic DNA sequences. In various embodiments, RNA transcripts 120 are transcribed from different genomic DNA sequences that are under operable control of different promoters. For example, transcription of at least one of the RNA transcripts 120 can be controlled by a pol III promoter, and transcription of at least another one of the RNA transcripts 120 can be controlled by a pol II promoter. In various embodiments, the one or more RNA transcripts 120 are transcribed from the same or similar genomic regions. For example, the one or more RNA transcripts 120 may be transcribed from similar transcription start sites of different cells.

In various embodiments, the non-uniform 5' ends 110 of the RNA transcripts 120 contain a target sequence of interest (e.g., a target sequence for sequencing). In various embodiments, the non-uniform 5' ends 110 of the RNA transcripts 120 comprise one or more of: 1) a barcode sequence, 2) a sequence transcribed from a genomic sequence comprising a gene edit, 3) a sequence transcribed from a genomic sequence comprising one or more mutations, or 4) a sequence corresponding to a transcription start site (TSS). In various embodiments, the non-uniform 5' ends 110 of the RNA transcripts 120 comprise two or more of: 1) a barcode sequence, 2) a sequence transcribed from a genomic sequence comprising a gene edit, 3) a sequence transcribed from a genomic sequence comprising one or more muta-tions, or 4) a sequence corresponding to a transcription start site (TSS). For example, the non-uniform 5' ends 110 of the RNA transcripts 120 can include a barcode sequence and a sequence transcribed from a genomic sequence comprising a gene edit or a mutation. Further details of these various embodiments are described herein. In various embodiments, the non-uniform 5' end of a RNA transcript comprises less than 100 nucleotide bases. In various embodiments, the non-uniform 5' end of a RNA transcript comprises less than 5, less than 10, less than 20, less than 30, less than 40, less than 50, less than 75, less than 100, less than 200, less than 300, less than 400, less than 500, less than 1000, less than 2000, less than 3000, less than 4000, or less than 5000 nucleotide bases.

Figure 1D:
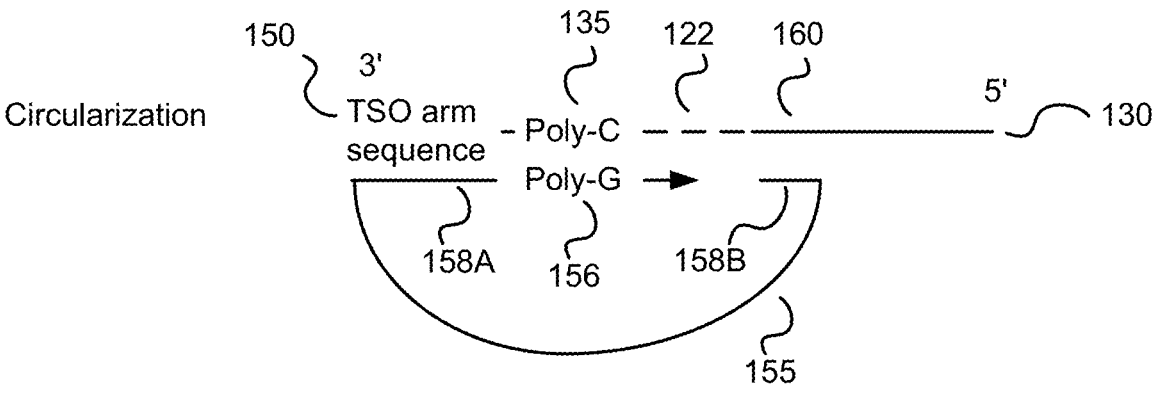

FIG. 1B shows a first stage of a construct comprising a single RNA transcript 120A and a corresponding cDNA strand 130. Although the description here (and subsequently in FIGS. 1C, 1D, and 1E) refers to a single RNA transcript 120A, the same methodology may be applied to other RNA transcripts (e.g., RNA transcript 120B, 120C, and 120D). At this stage, the RNA transcript 120A is reverse transcribed to generate a cDNA strand 130. For example, a reverse tran-scription primer and a reverse transcriptase (RT) enzyme are provided to initiate reverse transcription of the RNA tran-script 120A. An example reverse transcriptase is the Molo-ney murine leukemia (M-MLV) RT enzyme, although other known reverse transcriptase enzymes can be used.

At this first stage, the cDNA strand 130 includes a sequence 122 that is complementary to the non-uniform 5' end 110A of the RNA transcript 120A. Furthermore, the 3' end of the cDNA strand 130 includes a poly C sequence 135 left as a result of the reverse transcription process. As shown in FIG. 1B, the poly C sequence 135 is untemplated. In various embodiments, the poly C sequence comprises between 2 to 10 cytosine nucleobases. In various embodi-ments, the poly C sequence comprises between 2 to 9 cytosine nucleobases, between 2 to 8 cytosine nucleobases, between 2 to 7 cytosine nucleobases, between 2 to 6 cytosine nucleobases, between 2 to 5 cytosine nucleobases, or between 2 to 4 cytosine nucleobases. In particular embodi-ments, the poly C sequence comprises between 2 to 5 cytosine nucleobases.

FIG. 1C shows a second stage of a construct comprising the RNA transcript 120A and cDNA strand 130. Here, FIG. 1C shows binding of a RNA template switching oligonucle-otide (TSO) sequence 145, which includes a poly G sequence 140, at the 5' end of the RNA transcript 120A. Notably, the poly G sequence 140 hybridizes with the poly-C sequence 135 of the cDNA strand 130, but the poly G sequence 140 is not directly linked (e.g., not covalently linked) to the non-uniform 5' end 110A of the RNA tran-script 120A. Furthermore, FIG. 1C shows incorporation of a template switching oligonucleotide (TSO) arm sequence 150 at the 3' end of the cDNA strand 130.

In various embodiments, the poly G sequence 140 com-prises between 2 to 10 guanine nucleobases. In various embodiments, the poly G sequence 140 comprises between 2 to 9 guanine nucleobases, between 2 to 8 guanine nucle-obases, between 2 to 7 guanine nucleobases, between 2 to 6 guanine nucleobases, between 2 to 5 guanine nucleobases, or between 2 to 4 guanine nucleobases. In particular embodi-ments, the poly G sequence 140 comprises between 2 to 5 guanine nucleobases.

In various embodiments, the RNA TSO includes one or more locked nucleic acids (LNAs). A locked nucleic acid, also referred to as a bridged nucleic acid, is a modified RNA nucleotide in which the ribose moiety is modified with an extra bridge connecting the 2' oxygen and 4' carbon. Inclu-sion of one or more LNAs in the RNA TSO can contribute towards increased stability against enzymatic degradation. Further details of LNAs is described in Jepsen J S, et al. "Locked nucleic acid: a potent nucleic acid analog in therapeutics and biotechnology." Oligonucleotides. 2004; 14(2):130-46, which is incorporated by reference in its entirety. In various embodiments, the RNA TSO comprises a LNA at a 5' end of the RNA TSO. In various embodiments, the RNA TSO comprises a LNA at a 3' end of the RNA TSO. In various embodiments, between 1% and 50% of the nucleotides of the RNA TSO comprise locked nucleic acids. In various embodiments, between 1% and 40%, between 1% and 30%, between 1% and 20%, or between 1% and 10% of the nucleotides of the RNA TSO comprise locked nucleic acids.

In various embodiments, the progression from the first stage (shown in FIG. 1B) to the second stage (shown in FIG. 1C) is as follows: the RNA TSO 145 comprising a poly G sequence 140 is provided to the construct shown in FIG. 1B. The poly G sequence 140 hybridizes with the poly C sequence 135 of the cDNA strand 130. Further reverse transcription extension occurs using reverse transcriptase to generate the TSO arm sequence 150 which is complementary to a portion of the RNA TSO 145.

Reference is now made to FIG. 1D, which shows a construct comprising the cDNA strand 130 and a padlock probe 155. Moving from FIG. 1C to FIG. 1D involves contacting the cDNA strand 130 with the padlock probe 155. Here, the padlock probe 155 includes a first arm 158A which may optionally comprise a poly G sequence 156 and a second arm 158B. The poly G sequence 156 hybridizes with the poly C sequence 135 of the cDNA strand 130, a sequence of the first arm 158A hybridizes with the TSO arm sequence 150 of the cDNA strand 130, and a sequence of the second arm 158B hybridizes with a padlock arm sequence 160 of the cDNA strand 130.

Additionally, to generate the circular template comprising the padlock probe, methods involve extending a sequence of the padlock probe from the first arm 158A or optional poly G sequence 156 towards the second arm 158B, as indicated by the arrow in FIG. 1D. The extended sequence is complementary to sequence 122 of the cDNA strand 130 (e.g., sequence 122 that was complementary to the non-uniform 5' end 110A of the RNA transcript 120A). In various embodiments, the extension occurs by providing a DNA polymerase. An example DNA polymerase is a TaqIT DNA polymerase or a phi29 polymerase. Although, as one of skill in the art would appreciate, other known DNA polymerases can be used. In various embodiments, following extension, the extended sequence of the padlock probe is further ligated. For example, the extended sequence of the padlock probe is ligated to the second padlock arm 158B to complete the circularization. In various embodiments, the ligation is performed by providing a DNA ligase. An example DNA ligase is an Ampligase Thermostable DNA ligase, although other DNA ligases can be used.

Figure 1E:
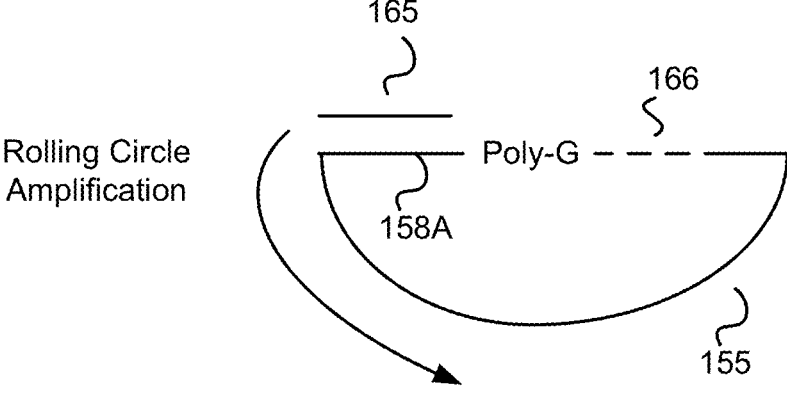

FIG. 1E shows the use of the circular template including the padlock probe 155 for performing nucleic acid amplification, such as rolling circle amplification (RCA). Here, the circular template now includes a sequence 166 that was extended and ligated in FIG. 1D. Here, sequence 166 represents the complement of sequence 122 in the cDNA strand (shown in FIG. 1D). In various embodiments, an amplification primer 165 may be provided such that the amplification primer 165 hybridizes with the first arm 158A of the padlock probe. In some embodiments, an amplification primer 165 is a portion of the cDNA strand 130. For example, the amplification primer 165 may be a sequence of the TSO arm sequence. In various embodiments, the TSO arm sequence may undergo digestion (e.g., digestion by an exonuclease) such that the amplification primer 165 remains behind. Digestion can be valuable to ensure that extension can occur beginning at the amplification primer 165. Here the end of the amplification primer 165 cannot have an overhang that is unbound to the first arm 158A.

As shown in FIG. 1E, the amplification primer 165 is hybridized with a sequence of the first arm 158A of the padlock probe 155. Thus, nucleic acid amplification may occur beginning at the amplification primer 165 located at the sequence of the first arm 158A. In some embodiments, the amplification primer 165 can be designed to hybridize with other sequences of the padlock probe 155. Therefore, initiation of nucleic acid amplification can begin at the amplification primer 165 hybridized at a different position of the padlock probe 155. Performing nucleic acid amplification results in the generation of multiple amplicons.

After FIG. 1E, the one or more amplicons generated via rolling circle amplification are sequenced to determine sequencing information. In particular embodiments, performing sequencing involves sequencing a single amplicon generated via rolling circle amplification. In some embodiments, commercial high-throughput digital sequencing techniques can be used, in which one or more amplicons are prepared for sequencing not one at a time, but in a bulk process, and where many sequences are read out preferably in parallel, or alternatively using an ultra-high throughput serial process that itself may be parallelized. In particular embodiments, the one or more amplicons are sequenced using in situ sequencing techniques. In various embodiments, sequencing of one or more amplicons is performed using fluorescence-based sequencing methods.

Figure 1F:
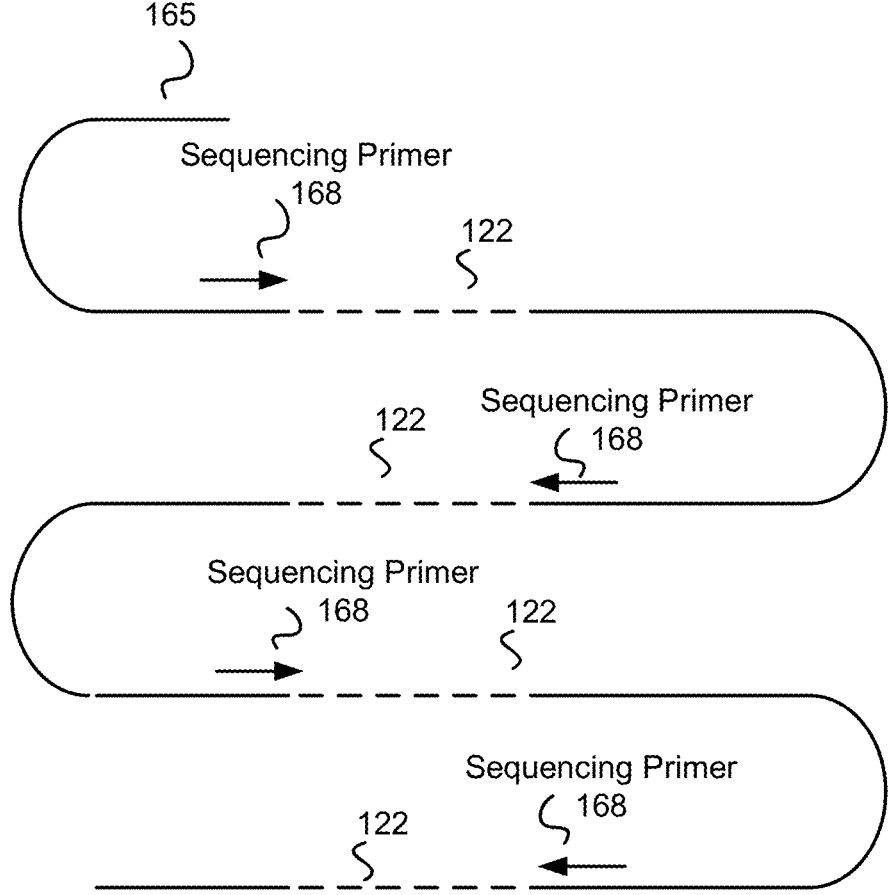

FIG. 1F shows a single amplicon generated via rolling circle amplification. Here, the amplicon can include a sequence of the amplification primer 165 at which rolling circle amplification was initiated. Furthermore, the amplicon can include multiple copies of the sequence 122 that is complementary to the non-uniform 5' end 110A of the RNA transcript 120A. Thus, by sequencing the amplicon (and in particular the multiple copies of the sequence 122), then a readout of the non-uniform 5' end of the RNA transcript 120A can be obtained. As shown in FIG. 1F, sequencing primers 168 can be provided to initiate sequencing (e.g., sequencing by synthesis) at the sequence 122. Therefore, the multiple copies of the sequence 122 can be read out (e.g., in parallel when conducting sequencing by synthesis). Example in situ sequencing methods, such as sequencing by synthesis, are described in further detail herein.

FIG. 1G shows a flow diagram for performing in situ sequencing of RNA transcripts with non-uniform 5' ends, in accordance with an embodiment. Step 170 involves generating cDNA strands from RNA transcripts comprising non-uniform 5' ends by incorporating RNA template switching oligonucleotides at 5' ends of RNA transcripts, wherein a cDNA strand comprises a TSO arm sequence, a poly C sequence, and a padlock arm sequence. Step 175 involves contacting the cDNA strand with a padlock probe, wherein a first arm of the padlock probe hybridizes with the TSO arm sequence and/or a second arm of the padlock probe hybridizes with the padlock arm sequence. Step 180 involves generating a circular template comprising the padlock probe hybridized to the cDNA strand. Step 185 involves performing nucleic acid amplification using the circular template to generate one or more amplicons. Step 190 involves sequencing the one or more amplicons. The method shown in FIG. 1F is applicable for a variety of applications including for analyzing exogenous transcripts (e.g., identifying and determining phenotypic impact of a perturbation including a CRISPR perturbation or shRNA/siRNA/ASO perturbation), analyzing naturally occurring transcripts (e.g., measuring gene expression, detecting splicing events), and analyzing modified, naturally occurring transcripts (e.g., detecting mutations or gene edits).

In Situ Sequencing Using Exogenous Transcripts

In various embodiments, methods disclosed herein involve performing in situ sequencing of exogenous RNA transcripts. Generally, exogenous RNA transcripts, as used herein, refer to the introduction of one or more barcode sequences into one or more cells such that one or more of the resulting RNA transcripts include the barcode sequences. In one embodiment, a unique barcode sequence can be used for each cell. In particular embodiments, the barcode sequences are located at 5' ends of the RNA transcripts (hence, contributing to the non-uniform 5' ends of the RNA transcripts). For example, barcode sequences may be introduced into the genomic DNA of a cell. Therefore, when the genomic DNA sequence comprising the barcode sequence is transcribed, the resulting RNA transcripts include the barcode sequence, or a complement thereof. Subsequent processing and in situ sequencing of the barcode sequence enables identification of the relevant information associated with the barcode sequence.

Introduction of a Barcode Sequence

In various embodiments, a barcode sequence is introduced to a cell. In various embodiments, the barcode sequence is introduced and integrated into the genomic DNA of a cell. In various embodiments, the barcode sequence is introduced as part of a plasmid, which resides within the cell but does not integrate into the genomic DNA of the cell. In various embodiments, a plurality of barcode sequences are introduced to pooled cells. Thus, barcode sequences can be introduced to large numbers of cells in the pool simultaneously. Here, generating cells with hundreds to thousands of different perturbations in a pooled format can save researchers labor and time.

In various embodiments, barcode sequences are between 4 and 40 nucleotides. In various embodiments, barcode sequences are between 8 and 25 nucleotides. In various embodiments, barcode sequences may be between 8 and 20 nucleotides. In particular embodiments, barcode sequences may be between 10 and 15 nucleotides. In particular embodiments, barcode sequences may be 12 nucleotides.

Introduction of the barcode sequence represents a genetic change to the cell. In various embodiments, the cell may undergo one or more genetic changes, one of which is an insertion of the barcode sequence. Additional examples of one or more genetic changes include mutations (e.g., polymorphisms, single nucleotide polymorphisms (SNPs), single nucleotide variants (SNVs)), insertions, deletions, knock-ins, and knock-outs. Additional examples of the genetic changes include genetic changes that cause changes in gene expression (e.g., gene silencing/activation) or genetic changes that cause a change in epigenetic state (e.g., histone binding, DNA methylation). In particular embodiments, the genetic changes include at least one insertion, such as an insertion of a barcode sequence. In various embodiments, the barcode sequence is randomly inserted into a genomic location in the genomic DNA.

In various embodiments, the barcode sequence encodes for a functional sequence. As used herein, a functional sequence refers to a sequence that provides a perturbation to a cell. Thus, when the barcode sequence is transcribed, the resulting RNA transcript includes the functional sequence which provides a perturbation to the cell. In various embodiments, the barcode sequence encodes for a functional sequence that is associated with a perturbation, such as a genetic perturbation (e.g., a gene edit) or a transcriptional perturbation (e.g., a perturbation that modulates gene expression). For example, the barcode sequence may encode for a guide RNA sequence. Therefore, the resulting RNA transcript may function as a guide RNA that guides proteins (e.g., CRISPR Cas9 proteins) to a target site. Thus, in this example, sequencing the barcode sequence enables identification of the particular genetic perturbation (e.g., CRISPR Cas9 may cleave at the target site) or particular transcriptional perturbation (e.g., CRISPR activator or CRISPR interference modulates gene expression) that was applied to a cell.

Figure 2A:
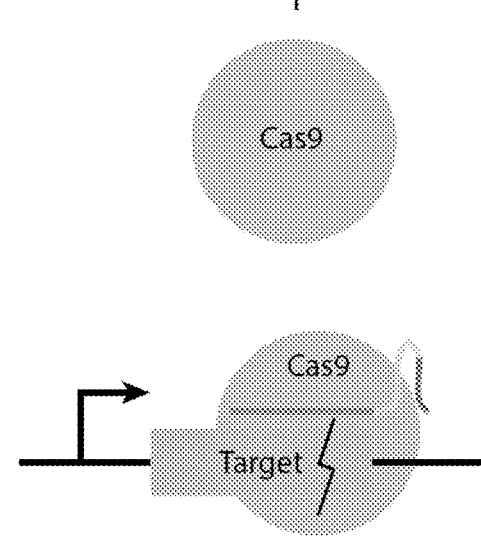
FIG. 2A shows an example schematic of a barcode sequence that encodes for a pol III guide RNA transcript.

Reference is briefly made to FIG. 2A, which shows an example schematic of a barcode sequence that encodes for a pol III guide RNA transcript. Specifically, FIG. 2A shows the expressed pol III guide RNA transcript that can combine with a protein (e.g., a Cas9 protein) and guide the protein to a target sequence. In various embodiments, the target sequence may be under the operable control of a promoter. At the target sequence, the Cas9 protein imparts a particular genetic perturbation (e.g., Cas9 may cleave at the target site).

As additional examples, the barcode sequence may encode for any of a small hairpin RNA (shRNA), a small interfering RNA (siRNA), or an antisense oligonucleotide (ASO). Therefore, the resulting RNA transcript may exhibit target binding exhibited by a shRNA, siRNA, or ASO. Thus, in these examples, sequencing the barcode sequence enables identification of the particular perturbation (e.g., shRNA, siRNA, or ASO) that was applied to a cell.

As another example, the barcode sequence may encode for a non-perturbing cell label (e.g., a label that identifies a source of a cell, an origin of the cell, a genetic background of the cell, and/or engineering processes applied to the cell). The use of non-perturbing cell labels can be useful when conducting pooled screening of a large number of varying cells (e.g., cells of different genetic backgrounds, different cell types, different cell lineages) in which cellular phenotypes are to be identified and then linked back to the barcode sequences of the large number of cells. In such embodiments, the use of non-perturbing cell labels allows pooled screening studies to be applied to cell lines with similar background genetics.

To provide an example, multiple populations of cells (e.g., cells from different sources/origins, genetic backgrounds, or cells exposed to different engineering processes) can be labeled with exogenous barcode sequences. For example, as disclosed herein, exogenous barcode sequences can be introduced into the genome of the cells (e.g., cells with differing genetic backgrounds). In various embodiments, methods can involve introducing different exogenous barcode sequences into 2 or more, 3 or more, 4 or more, 5 or more, 6 or more, 7 or more, 8 or more, 9 or more 10 or more, 11 or more, 12 or more 13 or more, 14 or more, 15 or more, 16 or more, 17 or more, 18 or more, 19 or more, 20 or more, 25 or more, 30 or more, 35 or more, 40 or more, 45 or more, 50 or more, 60 or more, 70 or more, 80 or more 90 or more, 100 or more, 150 or more, 200 or more, 250 or more, 300 or more, 350 or more, 400 or more, 450 or more, 500 or more, 600 or more, 700 or more, 800 or more, 900 or more, or 1000 or more populations of cells, where each barcode sequence serves as a non-perturbing cell label. The multiple populations of cells are combined into a pooled batch of cells for performing cellular phenotyping and cellular genotyping, as disclosed herein.

In various embodiments, using non-perturbing cell labels enables the high-throughput analysis and identification of interesting cellular phenotypes in large pooled populations of diverse cells, such as new cellular phenotypes that have not been previously observed or identified. Further details of analyzing cellular phenotypes are disclosed herein. Thus, these new cellular phenotypes can be linked to the exogenous barcode sequences that encode for non-perturbing cell labels (e.g., labels that identify any of a source of a cell, an origin of the cell, a genetic background of the cell, and/or processes applied to the cell). Thus, methods can involve attributing the new cellular phenotypes to any of a source of a cell, an origin of the cell, a genetic background of the cell, and/or engineering processes applied to the cell.

In various embodiments, the barcode sequence need not encode for a functional sequence. Instead, the barcode sequence can be associated with a sequence that encodes for the functional sequence. In various embodiments, both the barcode sequence and the associated sequence are simultaneously introduced to a cell. In various embodiments, the barcode sequence and the associated sequence are separately introduced to a cell. The barcode sequence may identify the associated sequence and therefore, subsequent sequencing of the barcode sequence enables the identification of the associated sequence and the corresponding functional sequence. As an example, the associated sequence may be a sequence that encodes for a guide RNA sequence. Thus, subsequent sequencing of the barcode sequence enables the identification of the guide RNA sequence (as well as the target site of the guide RNA sequence) and the corresponding perturbation. As additional examples, the associated sequence may encode for any of a small hairpin RNA (shRNA), a small interfering RNA (siRNA), an antisense oligonucleotide, or a non-perturbing cell label (e.g., a label that identifies a source or origin of a cell). Thus, subsequent sequencing of the barcode sequence enables the identification of any of the small hairpin RNA (shRNA), the small interfering RNA (siRNA), the antisense oligonucleotide, or the non-perturbing cell label.

In various embodiments, introducing barcode sequences that encode for a functional sequence may be advantageous. The sequencing of barcode sequences provides a direct readout of the perturbation provided to the cell. For example, in the scenario that the barcode sequence encodes for a guide RNA, the subsequent sequencing of the barcode sequence provides a direct quantifiable readout of the CRISPR targeting sequence. As another example, in the scenario that the barcode sequence encodes for a shRNA, a siRNA, or an ASO, the subsequent sequencing of the barcode sequence provides a direct quantifiable readout of the shRNA sequence, the siRNA sequence, or ASO sequence.

In various embodiments, cells may undergo one or more genetic changes in addition to introduction of a barcode sequence. For example, genetic changes can be introduction of one or more sequences, examples of which include a promoter sequence, a CRISPR scaffold, a Cas9 coding sequence, a padlock arm sequence (e.g., padlock arm sequence shown in FIG. 2B), and a reverse transcription primer sequence (e.g., for initiating reverse transcription using a reverse transcription primer). In various embodiments, any of the promoter sequence, CRISPR scaffold, Cas9 coding sequence, padlock arm sequence, and/or reverse transcription primer sequence can be randomly inserted into a genomic location in the genomic DNA. In various embodiments, any of the promoter sequence, CRISPR scaffold, Cas9 coding sequence, padlock arm sequence, and/or reverse transcription primer sequence can be randomly inserted simultaneously with the barcode sequence into a genomic location in the genomic DNA. For example, a single construct can be used to insert the barcode sequence and any of the promoter sequence, CRISPR scaffold, Cas9 coding sequence, padlock arm sequence, and/or reverse transcription primer sequence.

In various embodiments, one or more genetic changes, including a barcode sequence, are introduced using a particular cDNA. For example, a cDNA construct of a gene can be provided to the cell through a transfection method to introduce the one or more genetic changes. In various embodiments, the one or more genetic changes, including a barcode sequence, are introduced using a viral transfection (e.g., viral transduction) method. For example, viral transduction methods can involve lentiviral transfection, adenovirus transfection, or adeno-associated virus transfection. In particular embodiments, the one or more genetic changes are introduced using a lentiviral construct. For example, barcode sequences can be cloned into a lentiviral vector (e.g., via Golden Gate assembly) and introduced into the genomic DNA of cells. In particular embodiments, the lentiviral vector can further include one or more of a promoter sequence, a CRISPR scaffold, a padlock arm sequence, and a reverse transcription primer sequence (e.g., for initiating reverse transcription using a reverse transcription primer). In various embodiments, the barcode sequence is randomly inserted into genomic DNA using a lentiviral vector. In various embodiments, one or more of a promoter sequence, a CRISPR scaffold, a padlock arm sequence, and a reverse transcription primer sequence are randomly inserted into genomic DNA using a lentiviral vector. In various embodiments, the transfection method can involve a non-viral transfection method. For example, non-viral transfection methods can involve lipofectamine transfection or electroporation.

In various embodiments, the one or more genetic changes, including a barcode sequence, are introduced to a cell using Clustered Regularly Interspaced Short Palindromic Repeats (CRISPR). For example, a CRISPR system for generating one or more genetic changes in a cell can include a CRISPR complex (with a CRISPR enzyme), one or more guide sequences for hybridizing with a target sequence to direct sequence-specific binding of the CRISPR complex to the target sequence. Gene editing using CRISPR systems is further described in U.S. Pat. Nos. 8,697,359, 8,697,359; 8,771,945; 8,795,965; 8,865,406; 8,871,445; 8,889,356; 8,895,308; 8,906,616; 8,932,814; 8,945,839; 8,993,233; 8,999,641, WO2014093595, and WO2014093712 each of which is hereby incorporated by reference in its entirety. In particular embodiments, a CRISPR nuclease system is the CRISPR Cas9 system. Details regarding a CRISPR nuclease system, such as a CRISPR Cas9 system is described in WO2015071474, which is incorporated by reference in its entirety.

In various embodiments, the one or more genetic changes, include a barcode sequence, are introduced to a cell using Transcription Activator-like Effector Nuclease (TALENs). Gene editing using TALENS is further described in U.S. Pat. Nos. 9,353,378; 8,440,431; 8,440,432; 8,450,471; 8,586,363; 8,697,853; and 9,758,775, each of which is hereby incorporated by reference in its entirety.

In various embodiments, the one or more genetic changes, include a barcode sequence, are introduced to a cell using Zinc finger nucleases. Gene editing using Zinc finger nucleases is further described in U.S. Pat. Nos. 7,888,121, 8,409,861, 7,951,925, 8,110,379, and 7,919,313, each of which is hereby incorporated by reference in its entirety.

Example In Situ Sequencing of Barcode Sequences

Reference is now made to FIGS. 2B-2I, which show schematic diagrams for performing in situ sequencing of exogenous barcode sequences, in accordance with an embodiment. In particular, FIGS. 2B-2I differs from FIGS. 1A-1E in that RNA transcripts in FIGS. 2B-2I incorporate a sequence of an exogenous barcode. Specifically, the sequence of an exogenous barcode can be located on the non-uniform 5' end of a RNA transcript. In general, the description in relation to FIGS. 1A-IE similarly applies to the description here in relation to FIGS. 2B-2I.

Figures 2B, 2C:
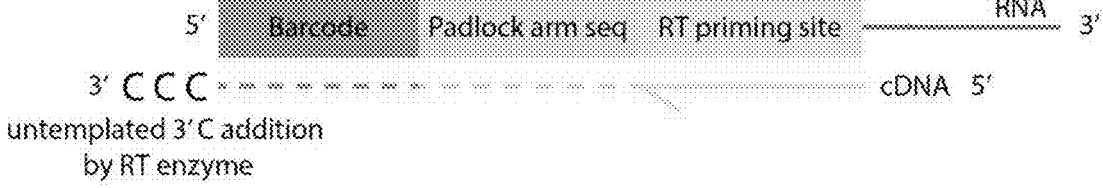
FIGS. 2B-2I show schematic diagrams for performing in situ sequencing using exogenous barcode sequences, in accordance with an embodiment.

Specifically, FIG. 2B shows an embodiment in which a barcode sequence, a padlock arm sequence, and a reverse transcription (RT) priming site have been inserted into the genomic DNA of a cell. Here, expression of the barcode sequence, the padlock arm sequence, and RT priming site are under the operable control of a promoter, such as a pol II or a pol III promoter. In various embodiments, the barcode sequence, the padlock arm sequence, and RT priming site are inserted into genomic DNA of a cell at a location that is less than 100, less than 50, less than 25, less than 20, less than 15, less than 10, or less than 5 nucleobases downstream of the promoter (e.g., a pol II or pol III promoter). During transcription, RNA transcripts are generated that include the complement of the barcode sequence, padlock arm, and RT priming site. Therefore, RNA transcripts are transcribed from a genomic sequence located less than 100, less than 50, less than 25, less than 20, less than 15, less than 10, or less than 5 nucleobases downstream of a promoter (e.g., a pol II or pol III promoter).

Although FIG. 2B shows a single genomic site, different barcode sequences may be introduced and integrated into the genomic DNA at other sites. For example, in addition to the first genome site shown in FIG. 2B, the genomic DNA may have at least a second genomic site at which a barcode sequence, padlock arm sequence, and RT priming site are inserted. In various embodiments, the expression at the first genomic site and the expression at the second genomic site may be under operable control of different promoters. For example, expression of the first genomic site may be under the operable control of a pol II promoter whereas the expression of the second genomic site may be under operable control of a pol III promoter, or vice versa.

As described herein, the barcode sequence may encode for, or may be associated with another sequence that encodes for a functional sequence. In some scenarios, the barcode sequence encodes for any of a guide RNA (gRNA), a small hairpin RNA (shRNA), a small interfering RNA (siRNA), an antisense oligonucleotide, or a non-perturbing cell label. In some scenarios, the barcode sequence is associated with another sequence that encodes for a functional sequence. Although not shown in FIGS. 2A-2H, an associated sequence may be inserted at a different genomic location. Therefore, the barcode sequence and the associated sequence can be separately expressed. In such embodiments, the barcode sequence serves as a surrogate readout for the associated sequence and corresponding perturbation.

FIG. 2C shows the generation of a cDNA strand by reverse transcribing a RNA transcript. Here, reverse transcription is initiated by priming at the RT priming site, followed by extension. As shown in FIG. 2C, the cDNA strand includes, at the 3' end, an untemplated poly C sequence which is a byproduct of the reverse transcription.

Figure 2D:
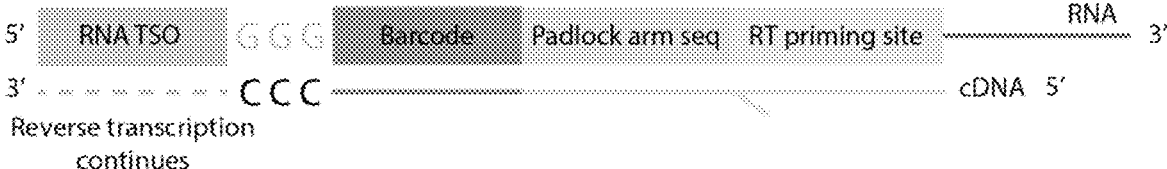

FIG. 2D shows the step of template switching to introduce a padlock arm sequence in the cDNA strand. Specifically, an oligonucleotide sequence comprising a RNA template switching oligonucleotide (TSO) sequence is provided to the RNA transcript/cDNA construct. In various embodiments, the RNA TSO comprises a poly G sequence. The poly G sequence hybridizes with the poly C sequence of the cDNA strand, leaving an untemplated portion of the RNA TSO sequence. In various embodiments, the RNA TSO includes one or more locked nucleic acids (LNAs). Reverse transcription continues by further extending the cDNA strand in the 5' to 3' direction. Here, the extension generates a sequence complementary to the RNA TSO sequence. This sequence complementary to the RNA TSO sequence is hereafter referred to as a "TSO arm sequence."

Figure 2E:
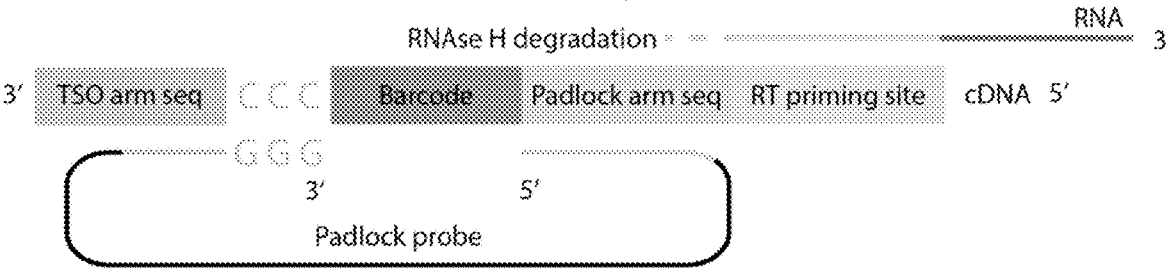

FIG. 2E introduces a padlock probe to the RNA/cDNA construct. In various embodiments, as shown in FIG. 2E, an enzyme is introduced to degrade the RNA transcript. In various embodiments, the enzyme is a RNAse enzyme. In particular embodiments, the RNAse enzyme is one of RNAse A or RNAse H. Degrading the RNA transcript ensures that the RNA transcript does not interfere in subsequent reactions (e.g., nucleic acid amplification).

Referring to the padlock probe, as shown in FIG. 2E, the padlock probe does not include a sequence that is complementary to the barcode sequence. As described herein, RNA transcripts include non-uniform 5' ends. Here, the barcode sequence of the cDNA strand corresponds to the non-uniform 5' end of the RNA transcript. Thus, it would be difficult to design padlock probes that hybridize with different barcode sequences (and/or different sequences corresponding to non-uniform 5' ends of RNA transcripts). To avoid this problem, the padlock probe is designed with two arm sequences that hybridize with regions that are largely constant across different cDNA strands. Thus, in various embodiments, the same padlock probe sequence can be used for the various applications described herein, as long as the same TSO arm sequence and same padlock arm sequence are incorporated into the cDNA strand.

Specifically, a first arm of the padlock probe includes a poly G sequence and a sequence complementary to a portion of the TSO arm sequence of the cDNA strand. Thus, as shown in FIG. 2E, the first arm of the padlock probe hybridizes with the poly C sequence and further hybridizes with a portion of the TSO arm sequence. The second arm of the padlock probe is designed to include a sequence that is complementary to a padlock arm sequence of the cDNA strand.

Figure 2F:
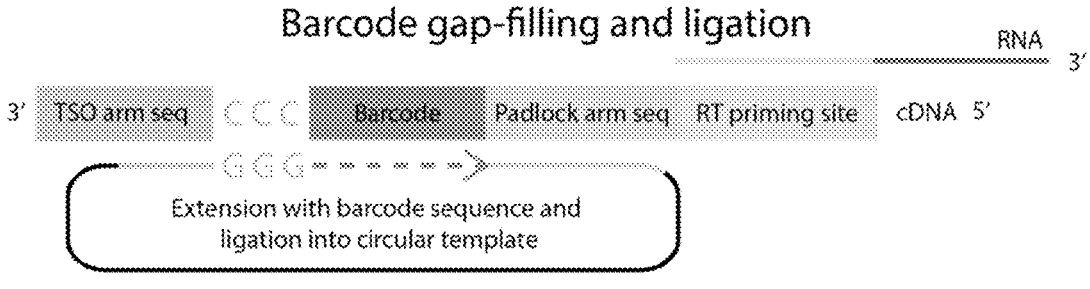

FIG. 2F shows the next step of barcode gap-filling and ligation to circularize the template including the padlock probe. Here, extension can be performed using a DNA polymerase such that a sequence complementary to the barcode sequence is generated. Then, DNA ligase is employed to ligate the sequence complementary to the barcode sequence to circularize the template. This circular template is now available for nucleic acid amplification.

Figure 2G:
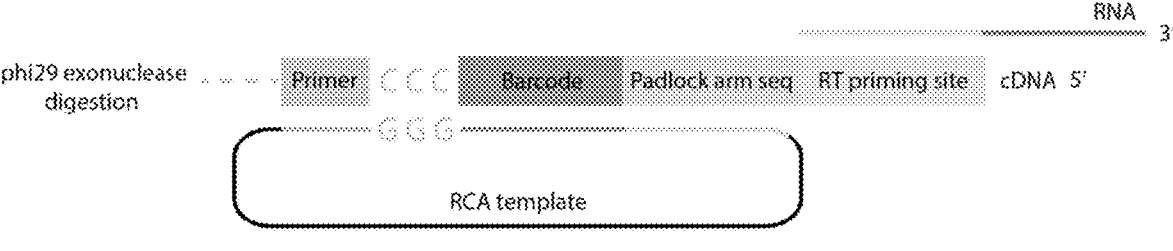

FIG. 2G shows one embodiment where the circular template (shown as the rolling circle amplification (RCA) template in FIG. 2F) is primed with a primer sequence. In the embodiment shown in FIG. 2G, the primer sequence may represent a portion of the original TSO arm sequence shown in FIG. 2F. For example, the TSO arm sequence may undergo digestion (e.g., exonuclease digestion by phi29 polymerase), leaving behind a primer sequence. In various embodiments, a separate primer sequence is designed and provided to hybridize with the circular template.

Figure 2H:
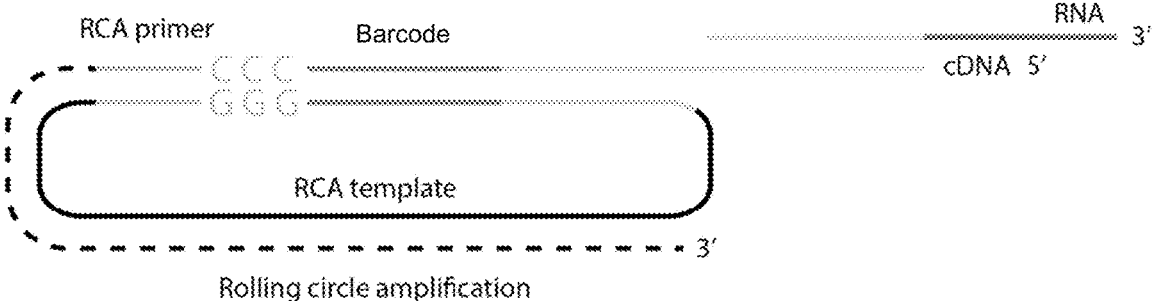
Figure 2I:
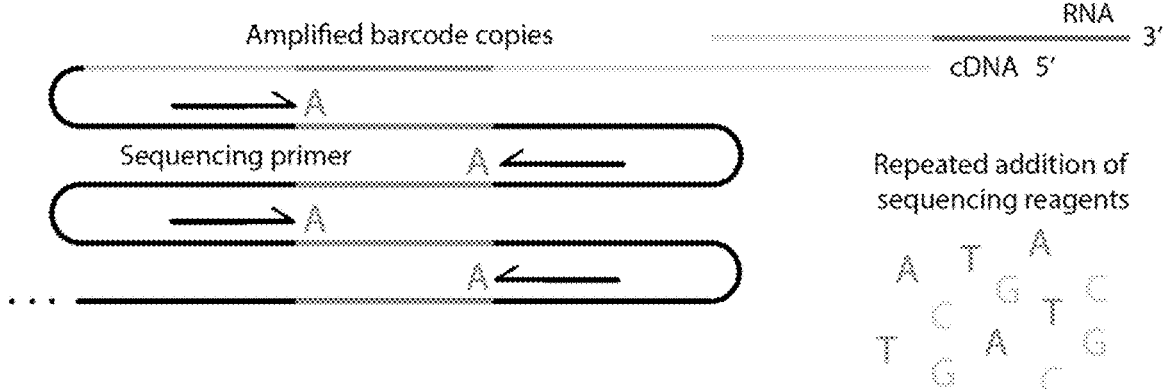

FIG. 2H shows the primer sequence (e.g., "RCA primer" in FIG. 2H) which serves as an initiating site for rolling circle amplification. Rolling circle amplification generates one or more amplicons, each of which includes the barcode sequence. In various embodiments, rolling circle amplification generates a single amplicon (e.g., a single continuous DNA strand with multiple copies of the barcode sequence). In various embodiments, rolling circle amplification generates two or more copies of amplicons. FIG. 2I shows an embodiment of in situ sequencing of the one or more amplicons. In this example, in situ sequencing can involve sequencing by synthesis. Fluorescently-tagged, reversibly terminated nucleotides are added and a fluorescent signal is captured, thereby reading out the nucleotide base at a particular position. This process is repeated for the subsequent position until sequencing of the one or more amplicons is completed.

In various embodiments, sequencing the one or more amplicons comprises sequencing a sequence of the exogenous barcode sequence. In one scenario, the barcode sequence identifies a corresponding perturbation, such as a guide RNA sequence, a shRNA, a siRNA, or an ASO. Therefore, a presence of a barcode sequence in a cell is indicative that the perturbation was applied to the cell. In another scenario, the barcode sequence represents a non-perturbing cell label (e.g., a label that identifies a source or origin of a cell). For example, for a pooled population of cells that includes multiple cell lines, a non-perturbing cell label can identify the cell line from which a cell originates. Therefore, sequencing a barcode sequence representative of a non-perturbing cell label indicates a cell line that the cell originates from.

Methods for Performing In Situ Sequencing of a Library in Pooled Screening

Embodiments disclosed herein, such as the methods described above in reference to FIGS. 1A-IE and/or FIGS. 2A-2H are useful for performing in situ sequencing of a gRNA library in pooled screening. Studying natural genetic variation in cells and inducing targeted perturbations are valuable steps for understanding protein function and biological pathways. Generating and examining cells with hundreds to thousands of different perturbations together in a pooled format can save researchers labor and time, as well as reducing batch effects from spatial separation of different cell lines. In such pooled screens, it is valuable to correlate the phenotype (the characteristic of interest) and the genotype (the perturbation made to a given cell) on a single-cell level, so that cells with the same perturbation can be analyzed for a common phenotype. As one solution, the genotypes of pooled cells can be read out while maintaining the morphology of the cells (e.g., for determining cellular phenotypes). This enables the linking of cellular genotypes and phenotypes for cells e.g., pooled cells. In various embodiments, a method for correlating genotypes and phenotypes of cells involves capturing, amplifying, and performing in situ sequencing of a region of interest (e.g., a non-uniform sequence) at the 5' end of a RNA transcript.

In various embodiments, methods disclosed herein are useful for in situ sequencing of gRNA library in a pooled CRISPR screen. Thus, resulting cellular phenotypes can be linked to particular CRISPR perturbations provided to the pooled cells. In various embodiments, methods disclosed herein are useful for in situ sequencing of a shRNA library in a pooled screen. Thus, resulting cellular phenotypes can be linked to particular shRNA perturbations provided to the pooled cells. In various embodiments, methods disclosed herein are useful for in situ sequencing of a siRNA library in a pooled screen. Thus, resulting cellular phenotypes can be linked to particular siRNA perturbations provided to the pooled cells. In various embodiments, methods disclosed herein are useful for in situ sequencing of an antisense oligonucleotide (ASO) library in a pooled screen. Thus, resulting cellular phenotypes can be linked to particular ASO perturbations.

Current in situ amplification and sequencing of gRNA libraries in pooled screening require RNA transcripts with constant regions flanking the variable region of interest, examples of which include RNA transcripts produced by RNA polymerase II (pol II). Example conventional in situ amplification and sequencing methods are described in Feldman et al., "Pooled Optical Screens in Human Cells,"

bioRxiv 383943, which is incorporated by reference in its entirety. Compared to RNA polymerase III (pol III) transcripts, pol II transcripts are more vulnerable to silencing, are not used directly for editing in CRISPR screens, and have fewer copies in cells, resulting in less robust cell identification.

Methods disclosed herein implement template switching during reverse transcription to add the upstream constant flanking sequence in the cDNA. A separate RNA template switch oligo (TSO) with a constant sequence of choice and a poly G sequence at the 3' end is introduced to bind to the untemplated poly C sequence tail formed by reverse transcriptase. The RT reaction then continues with the new template, effectively extending the cDNA with the missing padlock flanking sequence. This allows readout of RNA transcripts where the sequence of interest is at the beginning of the transcript (e.g., at the non-uniform 5' end of the RNA transcript), including pol III transcripts. Reading out pol III transcripts is valuable as these transcripts are very abundant due to rapid transcription reinitiation of the pol III complex. Increasing the number of matching transcripts that can be detected and amplified per cell also increases the confidence in barcode sequencing for that cell. This method also broadens the range of DNA designs to include those where the sequence of interest is immediately after a promoter.

As described herein, when performing in situ sequencing of a gRNA library in pooled screening, it is valuable to correlate the cellular phenotype with a corresponding cellular genotype (which reflects the perturbation made to a given cell). This provides an understanding of the phenotypic changes resulting from the perturbation.

Figure 3A:
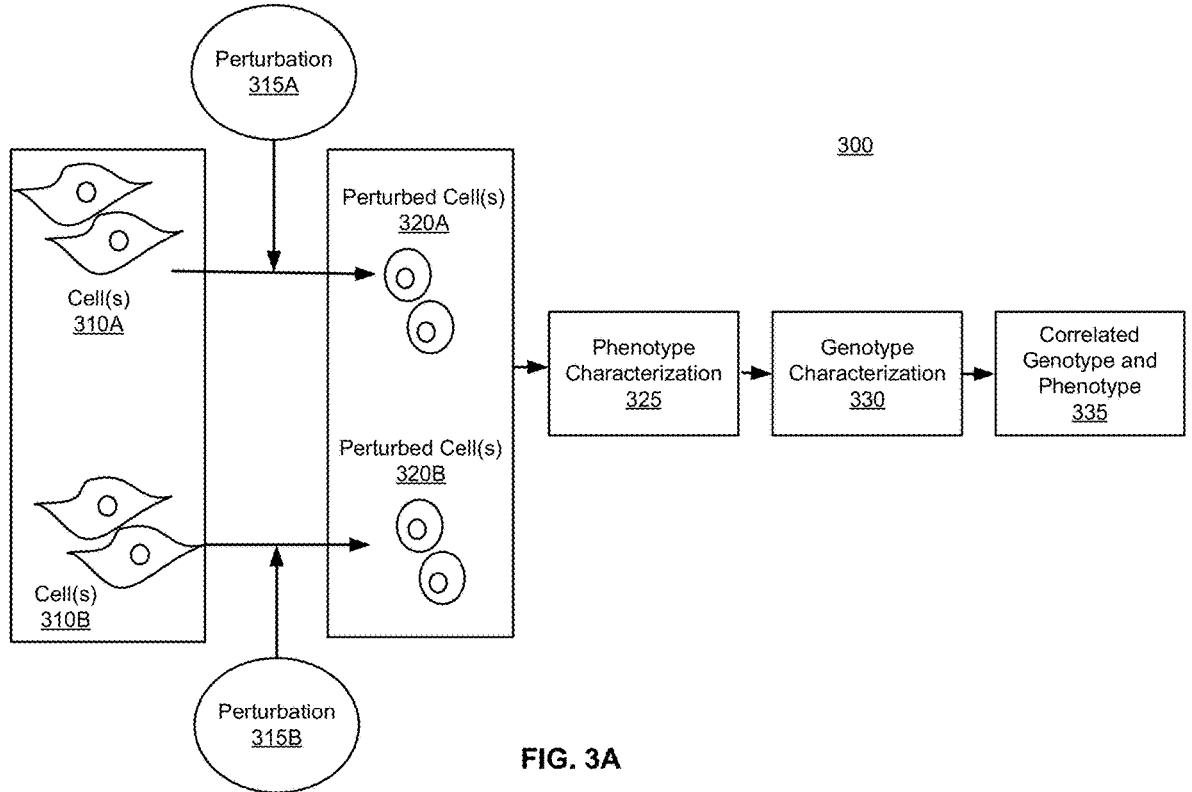
FIG. 3A depicts a flow process for correlating cellular genotypes and phenotypes, in accordance with an embodiment.

FIG. 3A depicts an overall system environment 300 for correlating cellular genotypes and phenotypes, in accordance with an embodiment. As shown in FIG. 3A, the overall system environment 300 may include cell(s) 310, such as one or more cell(s) 310A and one or more cell(s) 310B. In various embodiments, although cells 310A and cells 310B are separately shown in FIG. 3A, cells 310A and cells 310B may represent a pooled batch of cells. Here, the cells in the pooled batch of cells can vary in regards to the number of cells, type of cells (single cell type, mixture of cell types), genetic background, and/or cell lineage (e.g., cells in differing stages of maturation or differing stages of disease progression).

Cells 310A and cells 310B undergo perturbations 315 (e.g., perturbation 315A or perturbation 315B). In various embodiments, the cells 310A and 310B are a pooled batch of cells and the perturbations 315 (e.g., perturbation 315A or perturbation 315B) are introduced simultaneously. Although FIG. 3A shows two groups of cells 310A and 310B that receive two different perturbations 315A and 315B, in various embodiments, there may be additional cells and additional perturbations. In various embodiments, at least 2, at least 3, at least 4, at least 5, at least 10, at least 20, at least 30, at least 40, at least 50, at least 60, at least 70, at least 80, at least 90, at least 100, at least 500, or at least 1000 different perturbations are introduced to the cells 310. In various embodiments, cells in the pooled batch may receive one of many possible perturbations. In various embodiments, cells in the pooled batch may receive fewer (e.g., zero) or additional (e.g., two or more) perturbations of the many possible perturbations.

In various embodiments, the perturbation 315 involves introducing a barcode sequence into genomic DNA of the cells 310. In various embodiments, a perturbation may comprise a genetic perturbation (e.g., a gene edit) or a transcriptional perturbation (e.g., a perturbation that modulates gene expression). Additional example perturbations may include CRISPR based gene editing, CRISPR activation (CRISPRa), CRISPR interference (CRISPRi), transcription factor mediated differentiator (e.g., a transcription factor cassette), a shRNA, a siRNA, and an ASO.

In various embodiments, the perturbation 315 involves both introducing a barcode sequence into genomic DNA of the cells 310 and providing additionally one of CRISPR based gene editing, CRISPR activation (CRISPRa), CRISPR interference (CRISPRi), a transcription factor mediated differentiator (e.g., a transcription factor cassette), a shRNA, a siRNA, and a ASO. For example, a barcode sequence is introduced into genomic DNA of a cell and encodes for, or is associated with a sequence that encodes for, a guide RNA sequence. Thus, during transcription, the guide RNA sequence is transcribed. The guide RNA sequence binds and guides a CRISPR Cas9 protein to a target site. The CRISPR Cas9 can cleave at the target site, thereby imparting a gene edit at the target site. As another example, assuming the protein exhibits CRISPR activation (CRISPRa) activity, the protein is guided to the target site via the guide RNA and increases expression of genes of interest (e.g., by binding to transcriptional activators at the target site). As another example, assuming the protein exhibits CRISPR interference (CRISPRi) activity, the protein is guided to the target site via the guide RNA and decreases expression of genes of interest (e.g., by sterically blocking transcriptional initiation). Further details regarding CRISPRi and CRISPRa and methods for transcriptional modulation using CRISPRi/a is described in U.S. application Ser. No. 15/326,428 (now granted as U.S. Pat. No. 11,254,933) and PCT/CN2018/117643 (published as WO 2019120046), both which are hereby incorporated by reference in their entirety.

As another example, a barcode sequence is introduced into genomic DNA of a cell and encodes for, or is associated with a sequence that encodes for a shRNA. Thus, during transcription, the shRNA sequence is transcribed and can recruit the RNA-induced silencing complex (RISC) for degrading target mRNA. As another example, a barcode sequence is introduced into genomic DNA of a cell and encodes for, or is associated with a sequence that encodes for, a siRNA. Thus, during transcription, the siRNA sequence is transcribed and can also recruit the RNA-induced silencing complex (RISC) for degrading target mRNA. As another example, a barcode sequence is introduced to a cell and encodes for, or is associated with a sequence that encodes for, an ASO. Thus, during transcription, the ASO sequence is transcribed and can bind to target mRNA sequences, thereby reducing, restoring, or modifying protein expression.

Returning to FIG. 3A, in various embodiments, the exposure of the cells 310 to a perturbation 315 may result in a morphological change, as evidenced by the different appearance of the perturbed cells 320 (e.g., perturbed cells 320A and 320B). Here, the perturbed cells (e.g., perturbed cells 320A and perturbed cells 320B) can still represent a pooled batch of cells. The perturbed cells 320 undergo characterization, including both phenotype characterization 325 (e.g., to determine phenotypes of the perturbed cells 320) and genotype characterization 330 (e.g., to determine genotypes of the perturbed cells 320). Here, the morphology of the perturbed cells 320 is maintained for the phenotype characterization 325 while also enabling the genotype characterization 330. For example, perturbed cells 320 may undergo fixation and/or permeabilization such that phenotype characterization 325 can occur on the same cell population as the genotype characterization 330. Thus, the cellular phenotype and cellular genotype can be determined for each cell, thereby enabling the correlation between the determined cellular phenotype and cellular genotype.

Although FIG. 3A shows that the phenotype characterization 325 occurs prior to the genotype characterization 330, in various embodiments, the steps of the phenotype characterization 325 and the genotype characterization 330 may be differently ordered. For example, in some embodiments, the genotype characterization 330 is performed prior to the phenotype characterization 325. In some embodiments, the phenotype characterization 325 and the genotype characterization 330 are performed in parallel (e.g., simultaneously).

Example methods for performing genotype characterization 330 are described herein in reference to FIGS. 1A-1E and FIGS. 2A-2H. Specifically, performing the genotype characterization 330 involves performing in situ sequencing of exogenous barcodes. In particular embodiments, in situ sequencing of exogenous barcodes includes an imaging based sequencing in which individual nucleotide bases of the exogenous barcodes are captured. For example, performing in situ sequencing of exogenous barcodes can involve performing sequencing by synthesis to capture fluorescent signals of differently labeled nucleotide bases to readout the sequences of at least the exogenous barcodes.

By sequencing the barcode sequences, the corresponding perturbation provided to the cell can be identified. Using the determined sequence of the one or more amplicons, presence or absence of modulated expression (due to the perturbation) of a target gene can be determined. Thus, as shown in FIG. 3A, the genotypes and phenotypes of the cells can be correlated on the single-cell level, such that both genotypes and phenotypes are accurately attributed to individual cells.

Devices for Characterizing Cellular Phenotypes and Genotypes

In various embodiments, the genotype characterization 330 and/or the phenotype characterization 325 shown in FIG. 3A can involve the implementation of one or more devices. In various embodiments, an imaging device is employed for performing the phenotype characterization 325. Generally, the imaging device is a device that can capture, through non-destructive means, images of cells. Furthermore, the imaging device can resolve individual cells such that the phenotype of individual cells can be determined. In various embodiments, the imaging device can capture an image of cells, wherein the cells are cultured in an in vitro 2D culture, in vitro 3D culture, in vitro organoid or organ-on-chip systems, or ex vivo.

In various embodiments, the imaging device is capable of capturing a contrast image (e.g., an image based on differences in light intensity). Examples of a contrast image include any of a bright-field image, phase-contrast image, dark-field image, Rheinberg Illumination image, or polarization image. In various embodiments, the imaging device captures an immunofluorescence image. In various embodiments, the imaging device captures an immunocytochemistry image. Example imaging devices capable of capturing a contrast image, immunofluorescence image, or immunocytochemistry image include a light microscope, such as any of a brightfield microscope, darkfield microscope, phase-contrast microscope, differential interference contrast microscope, fluorescence microscope, confocal microscope, or two-photon microscope.

In various embodiments, a sequencing and imaging device is employed for performing the genotype characterization 330. In various embodiments, the imaging device used to perform the phenotype characterization 325 is the same device as the sequencing and imaging device used to perform the genotype characterization 330.

In particular embodiments, the sequencing and imaging device is a single device. For example, sequencing by synthesis can be performed using an imaging device that captures signals as individual nucleotide bases are incorporated, thereby reading out the sequence of an amplicon. In various embodiments, the sequencing and imaging device comprises an imaging modality with one or more, two or more, three or more, four or more, or five or more image sensors. As one example, the image sensor is a photomultiplier tube (PMT). As another example, the image sensor is a charge-coupled device (CCD). As another example, the image sensor is a Complementary metal-oxide-semiconductor (CMOS).

In various embodiments, the sequencing and imaging device comprises a color multiplexer for detection of one or more distinct colors of light. The light emitted from one or more fluorescent emitters is detected by a detector. In certain aspects, the detector is configured to detect photons of light with certain wavelengths. In various embodiments, the device contains one or more emission filters, excitation filters, and/or dichroics for directing certain wavelengths of light within the optical system.

In various embodiments, the sequencing and imaging device captures two or more colors of light in serial or in parallel. In particular embodiments, the different colors of light being detected are spaced along the electromagnetic spectrum to facilitate discrimination between the colors. For example, the fluorescence signals are spaced along the electromagnetic spectrum by emission wavelength to facilitate specific detection of certain fluorescent moieties. As another example, the fluorescence signals are spaced along the electromagnetic spectrum by excitation wavelength to facilitate specific excitation of certain fluorescent moieties. For example, when performing sequencing by synthesis, different nucleotide bases are labeled with different fluorescent tags and therefore, the capturing of a particular fluorescent signal corresponds to a specific nucleotide base. In various embodiments, the colors of emission light are distributed around about 510 nm, 570 nm, 620 nm, and/or 680 nm. In various embodiments, the colors of excitation light are distributed around about 480 nm, 530 nm, 590 nm, and/or 640 nm.

Example Flow Process for Determining Cellular Genotype and Phenotype

Reference is now made to FIG. 3B, which depicts a flow process for determining cellular genotypes and phenotypes, in accordance with an embodiment.

Step 350 involves providing a perturbation to one or more cells. In particular embodiments, a perturbation is provided to a pooled population of cells. In various embodiments, a plurality of perturbations are provided to a pooled population of cells. Thus, in some embodiments, although the subsequent steps 355, 360, 362, 365, 370, 375, 380 and 385 may refer to a single cell, the steps may be performed for individual cells across a pooled population of cells.

Step 355 involves fixing and permeabilizing the cell. Step 355 may, in some embodiments, be an optional step, as indicated by the dotted lines in FIG. 3B. Fixing and permeabilizing the cell maintains the morphology of the cell (e.g., for determining the cellular phenotype) while the cellular genotype is determined.

Step 360 involves reverse transcribing a RNA transcript from the cell using at least a RNA template switching oligonucleotide sequence to generate a cDNA strand. Here, the cDNA strand comprises a TSO arm sequence, a barcode sequence, and a padlock arm sequence.

Step 362 involves determining a phenotype of the cell. Here, the morphology of the cell is maintained until step 362 and therefore, the phenotype of the cell is determined according to the maintained morphology of the cell. In various embodiments, determining a phenotype of the cell includes, but is not limited to, capturing an image that reveals the morphology of the cell, mechanical properties of the cell, the localization of proteins within each cell, cellular organelles or substructures, cell division status of each cell, localization or quantification of RNA within each cell via fluorescent in situ hybridization (FISH) or other means, cellular migration, live calcium imaging, cell-cell-interaction, or any other phenotyping assay. In some embodiments, analyzing the phenotype of a cell comprises performing an assay selected from the group of high content imaging, calcium imaging, immunohistochemistry, cell morphology imaging, protein aggregation imaging, cell-cell interaction imaging, live cell imaging, and any other imaging-based assay modality.

Step 365 involves contacting the cDNA strand with a padlock probe. Here, a first arm of the padlock probe hybridizes with the TSO arm sequence of the cDNA strand. Furthermore, a second arm of the padlock probe hybridizes with the padlock arm sequence of the cDNA strand.

Step 370 involves a gap filling step. Specifically, step 370 involves extending the padlock probe complementary to the barcode sequence to generate a circular template. Step 375 involves using the circular template to perform nucleic acid amplification. In various embodiments, the nucleic acid amplification process involves a rolling circle amplification process.

Although FIG. 3 shows that step 362 (determining phenotype of the cell) occurs subsequent to step 360 (performing nucleic acid amplification), in various embodiments, the step 362 of determining phenotype of the cell can be performed in a different order relative to the steps shown in FIG. 3B. For example, in various embodiments, step 362 is performed after step 375. In various embodiments, step 362 is performed between steps 375 and 380.

Step 380 involves sequencing at least a barcode sequence to determine the genotype of the cell. In various embodiments, the sequencing involves performing in situ sequencing. Here, in situ sequencing involves a microscopy-based readout that images one base at a time.

In some embodiments, step 362 (determining phenotype) can be performed in parallel with step 380 (sequencing). In various embodiments, step 362 (determining phenotype) can be performed prior to step 380 (sequencing). In various embodiments, step 362 (determining phenotype) can be performed subsequent to step 380 (sequencing).

Step 385 involves correlating the cell genotype with the cell phenotype. In such pooled screens, it is valuable to correlate the phenotype (the characteristic of interest) and the genotype (the perturbation made to a given cell) on a single-cell level, so that cells with the same perturbation can be analyzed for a common phenotype In Situ Sequencing Using Naturally Occurring Transcripts Methods disclosed herein are useful for performing in situ sequencing of naturally occurring RNA transcripts. In various embodiments, naturally occurring RNA transcripts may be a measure of gene expression and therefore, by performing in situ sequencing of the RNA transcripts, the expression of target genes can be qualitatively or quantitatively determined.

Returning to the example shown in FIGS. 1A-IE, RNA transcripts 120 shown in FIG. 1A may be naturally occurring RNA transcripts. For example, a first RNA transcript 120A may be transcribed from a first gene sequence, a second RNA transcript 120B may be transcribed from a second gene sequence, a third RNA transcript 120C may be transcribed from a third gene sequence, and a fourth RNA transcript 120D may be transcribed from a fourth gene sequence. Given that RNA transcripts 120 are transcribed from different genomic DNA sequences, the 5' ends of the RNA transcripts 120 differ from one another. In various embodiments, one or more of the RNA transcripts 120 may be independently transcribed from a genomic sequence located less than 100, less than 50, less than 25, less than 20, less than 15, less than 10, or less than 5 nucleobases downstream of a promoter (e.g., a pol II or pol III promoter). In particular embodiments, there may be differing numbers of copies of the first RNA transcript 120A, second RNA transcript 120B, third RNA transcript 120C, and fourth RNA transcript 120D. Thus, the methods shown in FIGS. 1A-IE are valuable for performing in situ sequencing to determine transcriptional expression of genes corresponding to the RNA transcripts 120.

In various embodiments, performing in situ sequencing of the RNA transcripts enables determination of the expression of a pre-defined set of target genes. For example, a pre-defined set of target genes may be included in a targeted gene panel. The one or more genes of the targeted panel may be genes that are known to be differentially expressed in the presence of a disease. Thus, by performing in situ sequencing of RNA transcripts from the one or more genes, the expression profile of the one or more genes can be determined. In various embodiments, the expression profile of the one or more genes is valuable for determining presence or absence of a disease.

For a targeted gene panel, reverse primers can be designed to hybridize with RNA transcripts that possess known sequences of the one or more genes of the targeted gene panel. For example, returning again to FIG. 1A, assume that the first RNA transcript 120A was transcribed from a sequence of a gene that is included in the targeted gene panel. However, RNA transcripts 120B, 120C, and 120D were transcribed from sequences of genes that are not included in the targeted gene panel. Thus, as shown in FIG. 1B, a specifically designed reverse primer hybridizes with the RNA transcript 120A, followed by extension by reverse transcriptase to generate the corresponding cDNA strand 130. The RNA transcripts 120B, 120C, and 120D are not primed and therefore, no reverse transcription occurs for those RNA transcripts. Thus, the subsequent steps shown in FIGS. 1C, 1D, 1E can take place for RNA transcript 120A, but does not take place for RNA transcripts 120B, 120C, and 120D.

For RNA transcripts that are transcribed from a gene in the targeted gene panel, the steps of template switching (FIG. 1C), circularization (FIG. 1D), and rolling circle amplification (FIG. 1E) are performed. Following rolling circle amplification, the one or more amplicons undergo sequencing. By sequencing the one or more amplicons, nucleotide sequences of the amplicons are determined. In particular embodiments, sequencing the one or more amplicons including performing sequencing of a sequence corresponding to the original RNA transcript (e.g., RNA transcript 120A), or a complement thereof. In various embodiments, the determined sequence can be compared to a reference genome or reference transcriptome (e.g., a set of reference transcripts) to identify the corresponding gene.

In various embodiments, the expression of a gene can be determined based on the quantity of one or more amplicons identified as having a sequence corresponding to the gene. For example, when performing fluorescent in situ sequencing (FISSEQ), the quantity of one or more amplicons with the sequence can be based on the fluorescence intensity captured during sequencing.

In various embodiments, naturally occurring RNA transcripts may include unique sequences that enable differentiation of cells and/or differentiation of cell populations. For example, unique sequences in cells and/or cell populations can include mutations (e.g., polymorphisms, single nucleotide polymorphisms (SNPs), single nucleotide variants (SNVs)). Therefore, a first cell or cell population may have a first set of mutations and a second cell or cell population may have a second set of mutations. Therefore, by performing in situ sequencing of naturally occurring RNA transcripts, the presence of the first set of mutations and the second set of mutations can be detected and used to differentiate between cells and/or cell populations. In various embodiments, different cells and/or cell populations may have different origins, different genetic backgrounds, and/or may have been exposed to different engineering processes. Thus, in situ sequencing of naturally occurring RNA transcripts with unique sequences can be useful when conducting pooled screening of a large number of varying cells (e.g., cells of different genetic backgrounds, different cell types, different cell lineages).

In various embodiments, multiple populations of cells (e.g., cells from different sources/origins, genetic backgrounds, or cells exposed to different engineering processes) can have different sets of mutations. In various embodiments, methods can involve performing in situ sequencing of 2 or more, 3 or more, 4 or more, 5 or more, 6 or more, 7 or more, 8 or more, 9 or more 10 or more, 11 or more, 12 or more 13 or more, 14 or more, 15 or more, 16 or more, 17 or more, 18 or more, 19 or more, 20 or more, 25 or more, 30 or more, 35 or more, 40 or more, 45 or more, 50 or more, 60 or more, 70 or more, 80 or more 90 or more, 100 or more, 150 or more, 200 or more, 250 or more, 300 or more, 350 or more, 400 or more, 450 or more, 500 or more, 600 or more, 700 or more, 800 or more, 900 or more, or 1000 or more populations of cells, where each population of cells can be distinguished from other populations of cells based on a naturally occurring unique sequence (e.g., one or more mutations). The multiple populations of cells are combined into a pooled batch of cells for performing cellular phenotyping and cellular genotyping, as disclosed herein.

Additionally, methods disclosed herein can involve performing in situ sequencing of naturally occurring RNA transcripts to determine transcription start sites. A transcription start site (TSS) is a genomic location where the first DNA nucleotide is transcribed into RNA. Understanding a location of a TSS is valuable for a variety of purposes including for mapping a 5' end of a gene, determining gene structure, predicting and locating a promoter of a gene, and understanding roles of regulatory elements (e.g., promoter, enhancer, transcription factors) that may bind near the TSS for initiating transcription. Thus, precisely mapped transcription start sites can be a valuable resource for understanding regulatory transcriptional networks.

Generally, performing in situ sequencing to determine a transcription start site (TSS) involves performing the steps shown in FIGS. 1A-IE. Referring to FIG. 1A, RNA transcripts 120 with non-uniform 5' ends may include a sequence corresponding to a TSS. As an example, the 5' end of the RNA transcript may comprise the TSS. Specifically, RNA transcripts with non-uniform 5' ends undergo reverse transcription (FIG. 1), followed by template switching (FIG. 1C), template circularization (FIG. 1D), and rolling circle amplification (FIG. 1E). One or more amplicons generated via the rolling circle amplification are sequenced e.g., via in situ sequencing methods such as fluorescent in situ sequencing.

A transcription start site can be determined using the sequences of the one or more amplicons. For example, an amplicon may have a sequence that is derived from a non-uniform 5' end of a RNA transcript. Here, the non-uniform 5' end of a RNA transcript can include the first RNA nucleotide that was transcribed from genomic DNA. Thus, by sequencing the amplicon, the sequence at the 5' end of the RNA transcript can be mapped to a TSS.

Additionally, methods disclosed herein can involve performing in situ sequencing of naturally occurring RNA transcripts to determine one or more splice events. In various embodiments, a splice event can include any of an exon junction, splice variant, a fusion, an intra-genic rearrangement, a deletion, an insertion, a novel/extended exon, a novel exon junction substitution, or a retained intron.

RNA splicing is a process in molecular biology where precursor messenger RNA (pre-mRNA) transcripts are transformed into mature messenger RNA (mRNA) transcripts. Specifically, a spliceosome recognizes and excises introns in pre-mRNA and further ligates the remaining exons to generate the mRNA transcript. Thus, a splice site can refer to a location in the RNA transcript where two exons were ligated (or where an intron was excised). Here, in situ sequencing of naturally occurring RNA transcripts enables identification of splice events (e.g., intron excisions and/or exon ligations). In various embodiments, methods disclosed herein can be valuable for identifying misspliced or alternatively spliced RNA transcripts. Alternative splicing refers to small differences in the splicing of pre-mRNA that can lead to different RNA transcripts. For example, a single pre-mRNA can be spliced in multiple different ways depending on which exons are retained. As a result, multiple distinct mature mRNAs are produced, which translate into different proteins with distinct structures. Consequently, the proteins translated from alternatively spliced mRNAs will contain differences in their amino acid sequence and, often, in their biological functions.

Generally, performing in situ sequencing to determine one or more splice sites involves performing the steps shown in FIGS. 1A-IE. Referring to FIG. 1A, RNA transcripts 120 with non-uniform 5' ends may include a splice site. Specifically, RNA transcripts with non-uniform 5' ends undergo reverse transcription (FIG. 1B), followed by template switching (FIG. 1C), template circularization (FIG. 1D), and rolling circle amplification (FIG. 1E). One or more amplicons generated via the rolling circle amplification are sequenced e.g., via in situ sequencing methods such as fluorescent in situ sequencing.

To detect splice sites, sequences of one or more amplicons may be aligned to a reference genome. In scenario where a mature RNA transcript is composed of two exons that have been ligated by a spliceosome, a first portion of the mature RNA transcript corresponding to the first exon would map to a first location of the genome, whereas a second portion of the mature RNA transcript corresponding to the second exon would map to a second location of the genome, often thousands of base pairs away from the first location. This is indicative of a splice event in which an intron was excised and the resulting two exons were ligated. Thus, put more generally, using the determined sequence of the one or more amplicons, presence, absence, or expression levels of a splicing event can be determined.

In Situ Sequencing Using Modified, Naturally Occurring Transcripts

Methods disclosed herein can involve performing in situ sequencing of modified, naturally occurring RNA transcripts. In various embodiments, one or more of the modified, naturally occurring RNA transcripts 120 may be independently transcribed from a genomic sequence located less than 100, less than 50, less than 25, less than 20, less than 15, less than 10, or less than 5 nucleobases downstream of a promoter (e.g., a pol II or pol III promoter).

In some aspects, methods disclosed herein can involve performing in situ sequencing of RNA transcripts transcribed from genomic DNA that have undergone genetic editing. Thus, such methods may be useful for evaluating the efficiency or expression of the genetic edit. In particular embodiments, the genetic edit is introduced into genomic DNA at a location near a transcription start site (TSS). Thus, the genetic edit can be transcribed and included in a RNA transcript. Examples of genetic edits in the genomic DNA include any of mutations (e.g., polymorphisms, single nucleotide polymorphisms (SNPs), single nucleotide variants (SNVs)), insertions, deletions, knock-ins, and knock-outs.

In various embodiments, the genetic edit is introduced into genomic DNA at a location within 10 nucleotide bases of the TSS. In various embodiments, the genetic edit in introduced into genomic DNA at a location within 2 nucleotide bases, within 3 nucleotide bases, within 4 nucleotide bases, within 5 nucleotide bases, within 10 nucleotide bases, within 15 nucleotide bases, within 20 nucleotide bases, within 25 nucleotide bases, within 30 nucleotide bases, within 40 nucleotide bases, within 50 nucleotide bases, within 60 nucleotide bases, within 70 nucleotide bases, within 80 nucleotide bases, within 90 nucleotide bases, within 100 nucleotide bases, within 150 nucleotide bases, within 200 nucleotide bases, within 250 nucleotide bases, within 300 nucleotide bases, within 400 nucleotide bases, within 500 nucleotide bases, or within 1000 nucleotide bases of the TSS.

In various embodiments, a genetic edit can be introduced to the genomic DNA using a particular cDNA. In various embodiments, the genetic edit can be introduced into the genomic DNA via a viral transfection (e.g., viral transduction) method. Viral transduction methods can involve lentiviral transfection, adenovirus transfection, or adeno-associated virus transfection. In various embodiments, the transfection method can involve a non-viral transfection method. Non-viral transfection methods can involve lipofectamine transfection or electroporation. In various embodiments, the genetic edit is introduced to the genomic DNA using Clustered Regularly Interspaced Short Palindromic Repeats (CRISPR). In various embodiments, the genetic edit comprises one or more of a prime edit or a base edit. Further details of base editing and prime editing are described in Kantor et al., CRISPR-Cas9 DNA Base-Editing and Prime-Editing, Int. J. Mol. Sci. 2020 September; 21(17): 6240, which is hereby incorporated by reference in its entirety. In various embodiments, the genetic edit is introduced into the genomic DNA using Transcription Activator-like Effector Nuclease (TALENs). In various embodiments, the genetic edit is introduced into the genomic DNA using Zinc finger nucleases.

Generally, performing in situ sequencing of RNA transcripts transcribed from genomic DNA that have undergone genetic editing involves performing the steps shown in FIGS. 1A-IE. Referring to FIG. 1A, RNA transcripts 120 with non-uniform 5' ends may include a sequence transcribed from a genomic sequence comprising one or more gene edits. For example, the one or more genetic edits were introduced into genomic DNA, and given the proximity of the one or more genetic edits to the TSS, the one or more genetic edits may be transcribed and present in the RNA transcripts. In various embodiments, the one or more genetic edits may be located within the non-uniform 5' end. In various embodiments, the one or more genetic edits may be present in the RNA transcript, but is outside the non-uniform 5' end. The RNA transcripts undergo reverse transcription (FIG. 1B), followed by template switching (FIG. 1C), template circularization (FIG. 1D), and rolling circle amplification (FIG. 1E). Thus, the one or more genetic edits present in the RNA transcript are propagated through these processes to the resulting one or more amplicons. These one or more amplicons generated via the rolling circle amplification are sequenced e.g., via in situ sequencing methods such as fluorescent in situ sequencing. Thus, sequencing the one or more amplicons enables detection of presence or absence of one or more genetic edits.

As another example, methods disclosed herein can involve performing in situ sequencing of RNA transcripts to identify one or more mutations occurring in genomic DNA near the transcription start site (TSS). Thus, such methods may be useful for identifying the presence of the one or more mutations in the genomic DNA near the TSS. In various embodiments, mutations comprise any of a single nucleotide variant (SNV), a single nucleotide polymorphism (SNP), a copy number variation (CNV), an insertion, a deletion, a duplication, an inversion, or a translocation.

Generally, performing in situ sequencing of RNA transcripts to identify one or more mutations occurring in genomic DNA near the transcription start site (TSS) involves performing the steps shown in FIGS. 1A-IE. Referring to FIG. 1A, RNA transcripts 120 with non-uniform 5' end may comprise a sequence transcribed from a genomic sequence comprising one or more mutations. Given the proximity of the one or more mutations to the TSS, the one or more mutations may be transcribed and present in the RNA transcripts. In various embodiments, the one or more mutations may be located within the non-uniform 5' end. In various embodiments, the one or more mutations may be present in the RNA transcript, but outside the non-uniform 5' end. The RNA transcripts undergo reverse transcription (FIG. 1B), followed by template switching (FIG. 1C), template circularization (FIG. 1D), and rolling circle amplification (FIG. 1E). Thus, the one or more mutations present in the RNA transcript are propagated to the resulting one or more amplicons. These one or more amplicons generated via the rolling circle amplification are sequenced e.g., via in situ sequencing methods such as fluorescent in situ sequencing. Thus, using the sequences of the one or more amplicons, the presence or absence of the one or more mutations is detected.

Cells

In various embodiments, RNA transcripts with non-uniform 5' ends, as described in FIG. 1A, are derived from cells, such as cells 310A or cells 310B shown in FIG. 3A. In various embodiments, the cells are a population of cells. In various embodiments, the cells are multiple populations of cells. In various embodiments, the cells refer to a single cell. In particular embodiments, the cells represent a pooled batch of cells (e.g., useful for performing pooled optical screening). The cell(s) can vary in regards to the type of cells (single cell type, mixture of cell types), cell lineage (e.g., cells in differing stages of maturation or differing stages of disease progression), or culture type (e.g., in vitro 2D culture, in vitro 3D culture, in vitro organoid or organ-on-chip systems, or ex vivo). In various embodiments, the cells are obtained from a donor (e.g., a human donor). In various embodiments, the cells are diseased cells, such as cancer cells. In various embodiments, the cells are primary cells.

In particular embodiments, cells (e.g., cells 310A or cells 310B described in FIG. 3A) may vary in regards to the perturbation (e.g., perturbation 315A or perturbation 315B) that is provided to the cells. In various embodiments, cells may vary regarding the type and/or number of genetic edits made to the cell. For example, different exogenous barcodes can be introduced to the cells, where different exogenous barcodes encode for different guide RNA that direct CRISPR proteins to different target sites. Thus, different cells may undergo differential gene editing according to the exogenous barcode that is introduced into each of the different cells.

In various embodiments, the cells include at least 2, at least 3, at least 4, at least 5, at least 10, at least 20, at least 30, at least 40, at least 50, at least 60, at least 70, at least 80, at least 90, at least 100, at least 500, at least 1000, at least 2000, at least 3000, at least 4000, at least 5000, at least 10,000, at least 20,000, at least 30,000, at least 40,000, at least 50,000, at least 100,000, at least 200,000, at least 300,000, at least 400,000, at least 500,000, at least 750,000, at least 1 million, at least 2 million, at least 3 million, at least 4 million, at least 5 million, at least 6 million, at least 7 million, at least 8 million, at least 9 million, at least 10 million, at least 12 million, at least 15 million, at least 20 million, at least 30 million, at least 40 million, at least 50 million, at least 60 million, at least 70 million, at least 80 million, at least 90 million, or at least 100 million cells.

In various embodiments, the cells are any one of cells derived from the ectoderm layer, cells derived from the mesoderm layer, cells derived from the endoderm layer, embryonic stem cells, mesodermal cells, terminally differentiated cells, or pluripotent cells. In various embodiments, the cells are an in vitro culture of cells that are cultured in one or more devices that are conducive for imaging. Example devices include well plates, flasks, slides, and/or microfluidic devices. In various embodiments, the cells can be an in vitro culture of cells in one or more well plates (e.g., 6 well plate, 12 well plate, 24 well plate, 48 well plate, 96 well plate, 192 well plate, or 384 well plate). Such well plates, flasks, slides, and/or microfluidic devices can be configured (e.g., with clear bottom portions) for optical, fluorescence, or luminescence imaging.

In particular embodiments, the cells are induced pluripotent stem cells (iPSCs) that have undergone a reprogramming protocol. For example, iPSCs can be generated through a variety of methods including reprogramming somatic cells using reprogramming factors Oct4, Sox2, Klf4, and Myc. Reprogramming of somatic cells can occur through viral or episomal reprogramming techniques. Examples methods for generating iPSCs are further described in PCT/US2018/067679 (published as WO 2019133714), PCT/EP2009/003735 (published as WO2009144008), U.S. application Ser. No. 13/059,951 (published as US20110263015 and now abandoned), U.S. application Ser. No. 13/369,997 (now granted as U.S. Pat. No. 9,132,152), U.S. application Ser. No. 14/043,096 (published as US20140093486 and now abandoned), and U.S. application Ser. No. 13/441,328 (published as US20130266541 and now abandoned), each of which is hereby incorporated by reference in its entirety. In various embodiments, the cells are iPSCs in which the expression of certain transcripts are reduced or silenced. In various embodiments, transcripts that are reduced or silenced in iPSCs are pol II transcripts that are under the control of a pol II promoter. In various embodiments, transcripts that are reduced or silenced in iPSCs are pol III transcripts that are under the control of a pol III promoter.

In particular embodiments, the cells are differentiated cells (e.g., cells that have undergone a differentiation protocol). In various embodiments, the cells are differentiated from cells that previously exhibited pluripotency, examples of which include stem cells (e.g., embryonic stem cells or iPSCs). In various embodiments, the cells were differentiated from a primary cell (e.g., cells that underwent transdifferentiation).

In Situ Sequencing

Embodiments disclosed herein include performing in situ sequencing. Generally, in situ sequencing refers to the sequencing of nucleic acids in the preserved context of fixed cells and/or tissues. Thus, in situ sequencing enables the reading of sequences directly from intact cells and/or tissues, quantifies large numbers of mRNA transcripts simultaneously, and spatially resolves them with single-cell resolution. In situ sequencing can be applied for transcription expression profiling, splice variant mapping, mutation detection, and cellular genotyping (e.g., sequencing of barcode sequences to identify corresponding perturbations).

In various embodiments, cells or tissues are first fixed prior to performing sequencing to retain the spatial context of the cells or tissues. Example fixatives include crosslinkers such as formaldehyde, paraformaldehyde, and glutaraldehyde. Cells or tissues can further undergo a permeabilization step. Example reagents for permeabilization of cells or tissues include ethanol, methanol, acetone, saponin, Triton X-100, and Tween-20.

In various embodiments, in situ sequencing is fluorescent in situ sequencing (FISSEQ). FISSEQ combines the spatial context of RNA-FISH and the global transcriptome profiling of RNA-seq. FISSEQ involves preserving the cell and/or tissue, thereby enabling single molecule in situ RNA localization. Generally, FISSEQ involves a series of wet lab processing steps e.g., single-base polymerase extensions, which are performed on fixed cells or tissues. FISSEQ is analogous to sequencing by synthesis methods, except that FISSEQ is performed in situ (e.g., on fixed cells or tissues). Sequencing by synthesis is further described in U.S. Pat. Nos. 5,302,509 and 10,793,904, each of which is incorporated by reference in its entirety. In various embodiments, any sequencing methodology which relies on successive incorporation of nucleotides into a polynucleotide chain can be used. Suitable techniques in addition to FISSEQ include, for example, Pyrosequencing, MPSS (massively parallel signature sequencing) sequencing by synthesis, sequencing by ligation, sequencing by hybridization, and sequencing by cyclic reversible polymerization hybridization chain reaction (HCR).

In various embodiments, in situ sequencing involves the use of modified nucleotides that act as chain terminators. These modified nucleotides are also referred to as tagged, reversibly terminated bases. Once the modified nucleotide has been incorporated into the growing polynucleotide chain complementary to an amplicon sequence being sequenced, there is no free 3'-OH group available to direct further sequence extension. Once the nature of the base incorporated into the growing chain has been determined, the 3 block may be removed to allow addition of the next successive nucleotide. By ordering the products derived using these modified nucleotides, the sequence of the amplicon can be determined. In various embodiments, each of the modified nucleotides is labeled using a different label, known to correspond to the particular base, to facilitate discrimination between the bases added at each incorporation step. In various embodiments, modified nucleotides are labeled using fluorescent labels. Each nucleotide base type (e.g., adenine, thymine, guanine, cytosine) may carry a different fluorescent label. In some embodiments, the detectable label need not be a fluorescent label and any label which allows the detection of the incorporation of the nucleotide can be used.

In various embodiments, labels of the incorporated modified nucleotides are detected by using laser light of a wavelength specific for the labeled nucleotides, or the use of other suitable sources of illumination. For example, the fluorescence from the label on the nucleotide may be detected by a camera or other suitable detection means. In various embodiments, an entire sample can be imaged at each cycle to identify the fluorescent label, thereby identifying the incorporated nucleotide base. The fluorescent labels are then cleaved and washed away (e.g., via a stripping reagent which cleaves off base terminators and fluorophores), and the next cycle is initiated. The nucleotide sequence of each amplicon is thus read out in-situ via fluorescent microscopy. Further description of FISSEQ is detailed in Lee et al. "Fluorescent in situ sequencing (FISSEQ) of RNA for gene expression profiling in intact cells and tissues," Nature Protocols, 10, 442-458 (2015), which is incorporated by reference in its entirety.

EXAMPLES

Example 1: Example Methodologies for Determining Cellular Genotypes

The methods for genotyping a cell, as disclosed herein, were implemented to capture, amplify, and perform in situ sequencing of target regions. Here, the specific protocol for genotyping cells is as follows:

1) Preparing the samples for a perturbation screen proceeded as follows.
   a. Selection of genes to target in the CRISPR library and gRNA design for the given genes
   b. Synthesis of gRNA library and cloning of the gRNA into the lentiviral backbone containing promoter, CRISPR scaffold, and 3' padlock arm sequence. Here, only the 3' (downstream) arm sequence was needed, and this arm can be part of the CRISPR scaffold sequence when reading out CRISPR guide sequences.
   c. Infection of a Cas9-expressing cell culture (iPSCs, cancer lines, primary cells) with gRNA pool. Here, iPSCs and edited/differentiated cell lines with substantial silencing of pol II transcripts were used. Alternatively Cas9 and gRNAs may be simultaneously delivered using an all-in-one system.
   d. Experimentation (live imaging, chemical treatment, exposures) to target timepoint
2) Preparing samples for genotyping cells involved the steps as follows:
   a. Fixing of samples via paraformaldehyde and optional preservation of protein and RNA via 70% EtOH storage at −20 C
   b. EtOH permeabilization and gradual removal of EtOH via serial dilutions c. Hybridization of gRNA reverse transcription (RT) primer simultaneously with PFA and glutaraldehyde fixing for 30 minutes at room temperature d. Reverse transcription with an M-MLV RT enzyme (RevertAid) and corresponding buffer, RNA-based template switch oligonucleotide (TSO), dithiothreitol (DTT), betaine, MgCl2, dNTPs, and further addition of RT primer overnight at 37 C or 42 C i. Here, the template switch oligo (TSO) included the desired padlock sequence to be added, along with a 2-5 bp long homopolymer of G's at the 3' end. The TSO is composed of RNA (or mostly of RNA with LNA additions) so that it can be subsequently digested by RNAse H.

e. Paraformaldehyde/glutaraldehyde fixation of samples for 30 minutes at room temperature f. Samples were introduced to padlock probes and underwent Gap Fill via TaqIt, Ampligase, and RNAse H.

i. Two (or more) different padlock probes were introduced if a 5' flanking region had been integrated into the genome to amplify both pol II and pol III transcripts. One probe detected pol II transcripts and binds to the 5' and 3' constant regions in the genome, and the other probe detects pol III transcripts and binds to the TSO sequence and the 3' constant region in the genome.

g. Padlocked sequences were amplified via Rolling Circle Amplification (RCA) at 30 C overnight using phi29 polymerase (with or without a dedicated RCA primer)

h. Samples were imaged using cellular dyes, brightfield, quantitative phase contrast, or antibody staining to derive morphological phenotypes i. Samples were primed for gRNA sequencing by synthesis for 30 minutes at room temperature, using a sequencing primer with the same sequence as the padlock constant sequence upstream of the region to be sequenced i. Two or more different sequencing primers are used if a 5' flanking region has been integrated into the genome to amplify both pol II and pol III transcripts. One sequencing primer will match the pol II transcript amplicons, and the other primer will match the pol III transcript amplicons.

3) Steps of in situ sequencing involved the following:

a. 1 wash step b. Addition of pooled fluorescently-tagged, reversibly terminated base pairs, with 60 C incubation for 3 minutes with agitation c. 4× washes followed by 60 C incubation for 6 minutes with agitation d. Repeat of c.

e. 4× washes f. Addition of low concentration (1:200,000) Hoechst g. Samples are imaged via widefield fluorescence to capture the base pair of the gRNA at cycle X h. 1× wash i. Addition of stripping reagent to cleave off base terminators and fluorophores for 2 minutes at 60 C j. 3× washes followed by 60 C incubation for 2 minutes k. 2× washes As referred to in this Example, the designation of "SMASH RT chemistry, RNA TSO and padlock" refers to the example protocol described above, where at Step 2(d), the introduced TSO was composed of RNA (and no locked nucleic acids), and where at step 2(f), a single padlock probe was introduced (as opposed to two padlock probes).

As referred to in this Example, the designation of "SMASH RT chemistry, RNA TSO and both padlocks" refers to the example protocol described above, where at Step 2(d), the introduced TSO was composed of RNA (and no locked nucleic acids), and where at step 2(f), two padlock probes were introduced to amplify both pol II and pol III transcripts.

As referred to in this Example, the designation of "SMASH RT chemistry, RNA/LNA TSO and padlock" refers to the example protocol described above, where at Step 2(d), the introduced TSO was composed of RNA and LNAs, and where at step 2(f), a single padlock probe was introduced (as opposed to two padlock probes).

As referred to in this Example, the designation of "SMASH RT chemistry, RNA/LNA TSO and both padlocks" refers to the example protocol described above, where at Step 2(d), the introduced TSO was composed of RNA and LNAs, and where at step 2(f), two padlock probes were introduced to amplify both pol II and pol III transcripts.

These four experimental methodologies were compared to a representative conventional methodology (e.g., a positive control) referred to as "POSH RT chemistry and padlock." Here, the conventional in situ amplification and sequencing method is described in Feldman et al., "Pooled Optical Screens in Human Cells," bioRxiv 383943, which is incorporated by reference in its entirety. There, the method required constant regions flanking the variable region of interest, and only transcripts that include the upstream flanking region-produced by RNA polymerase II (pol II)—were detected. Due to the padlock probe binding step, this conventional method required two constant flanking sequences around the variable region to be transcribed to RNA, which was only possible if the sequence of interest was not at the beginning of the RNA transcript.

Reference is now made to FIGS. 4A and 4B, which show quantities of detected amplicons using the four different embodiments of the disclosed methodology, in comparison to the conventional methodology. Specifically, FIGS. 4A and 4B show plots with the quantified number of amplicons detected per reaction condition across two different in situ sequencing cycles. The first bar in each plot is the baseline POSH conditions (conventional method) with only pol II transcripts read out. The second and fourth bars represent 2 different SMASH conditions (embodiments of the method disclosed herein) with only pol III transcripts read out. The third and fifth bars represent two different SMASH conditions with both pol II and pol III transcripts read out. Altogether, each of the four different embodiments (e.g., 1) SMASH RT chemistry, RNA TSO and padlock, 2) SMASH RT chemistry, RNA TSO and both padlocks, 3) SMASH RT chemistry, RNA/LNA TSO and padlock, and 4) SMASH RT chemistry, RNA/LNA TSO and both padlocks) result in significant detected amplicons, indicating that cellular genotypes can be determined using these methodologies.

Example 2: SMASH Exhibits Increased Sensitivity Compared to POSH

Further studies were undertaken to determine the sensitivity of SMASH in comparison to POSH. As described herein, the disclosed methodologies (e.g., described in this example as "SMASH") can capture RNA pol III transcripts whereas conventional methods (e.g., described in this example as "POSH") require constant regions flanking a region of interest and therefore only capture RNA pol II transcripts (given that the promoter used to initiate RNA pol III does not allow for inclusion of a constant flanking region).

To evaluate sensitivity of the POSH and SMASH methods, A549 cells lentivirally infected with a CRISPR guide RNA targeting TGFBR1 were plated on a 6 well plate and fixed in paraformaldehyde (PFA), washed with PBS, permeabilized with 70% ethanol, and washed with PBST (PBS+0.05% Tween-20). RT primer was hybridized to the cells at room temperature before fixation in PFA and glutaraldehyde in PBST at room temperature. For "POSH" conditions, reverse transcription was performed overnight at 37 C in RevertAid RT enzyme, RevertAid RT buffer, dNTPs, BSA, RiboLock RNAse inhibitor, and RT primer. For "SMASH" conditions, reverse transcription was performed overnight at 37 C in SuperScript IV RT enzyme, RiboLock RNAse inhibitor, SuperScript IV RT buffer, DTT, betaine, MgCl2, RNA template switch oligo (TSOdNTPs, RT primer, and extra dCTP. Both conditions were incubated for the same duration and at the same temperature. After reverse transcription, the cells were washed 5× with PBST and lysed in Tris-HCl, pH 8.1, EDTA, and SDS lysis buffer at 65 C. Cells were cooled down to 37 C slowly and incubated at 37 C for 3 minutes before the addition of RNAse cocktail per 6-well plate well (Invitrogen, catalog number AM2286) and incubation at 37 C. Then, proteinase K were added to each well and cells were incubated in 37 C for 2 hours, followed by incubation at 95 C for 20 minutes to inactivate proteinase K. Samples were then SPRI selected and eluted in water. DNA concentration was measured with Qubit and all samples were diluted before qPCR. The "POSH" qPCR forward primer was designed to bind to a region upstream of the guide RNA sequence, including the entire 5' arm padlock sequence. The "SMASH" qPCR forward primer was designed to bind to the 5' region of the TSO binding site without the poly-C sequence. Both qPCR reactions shared the same reverse primer, which was designed to bind to the RT primer binding site and part of the gRNA scaffold downstream of the guide RNA sequence. Samples underwent qPCR with NEB Luna master mix in a QuantStudio qPCR machine with annealing and extension at 60 C. Average Ct values over three technical replicates were measured and converted to fold change.

FIG. 5 depicts the normalized Ct values for POSH and SMASH over the three technical replicates. In general, SMASH achieved 20-30 fold increased sensitivity in comparison to POSH. Here, the increased sensitivity is a measure of reverse transcription efficiency. Altogether, SMASH can enable detection and sequencing of pol III transcripts with 20-30 fold higher abundance than pol II transcripts, which can result in higher confidence in sequence accuracy for a given cell than previous methods that could only detect pol II transcripts.

The higher sensitivity of SMASH is likely due to the sgRNAs, being pol III transcripts, that are much more abundantly expressed in the cell than the counterpart expressed from the pol II transcript, which POSH detects. Additionally, because SMASH enables amplification and detection of transcripts with variable 5' ends (including pol III transcripts) that were undetectable by conventional methods, SMASH can enable spatially resolved mapping of these transcripts with single-cell resolution. Furthermore, SMASH and POSH are combinable methodologies for detecting both pol II transcripts and pol III transcripts, thereby further increasing sensitivity (and higher confidence in sequence accuracy).

The invention claimed is:

1. A construct for performing a rolling circle amplification reaction, the construct comprising:
an RNA transcript from a transfected cell, wherein the RNA transcript comprises a complementary sequence of a padlock arm sequence; and
a cDNA strand, wherein the cDNA strand is hybridized with the RNA transcript and is reverse transcribed from the RNA transcript,
wherein the cDNA strand comprises:
a template switching oligonucleotide (TSO) arm sequence;
a poly C sequence; and
a padlock arm sequence, wherein the transfected cell comprises the padlock arm sequence and is produced by inserting the padlock arm sequence into a genome of a cell using one of a construct of Clustered Regularly Interspaced Short Palindromic Repeats (CRISPR), a cDNA construct, a Transcription Activator-like Effector Nuclease (TALEN), and a Zinc finger nuclease; and
an RNA template switching oligonucleotide (TSO) comprising a poly G sequence,
wherein the RNA transcript is transcribed from the genome of the transfected cell
wherein the poly G sequence is hybridized to the poly C sequence of the cDNA strand, and wherein a portion of the RNA TSO is hybridized to the TSO arm sequence of the cDNA strand.

2. The construct of claim 1, wherein the cDNA strand further comprises a barcode sequence which encodes for a guide RNA (gRNA) that guides a CRISPR protein to a target site in genomic DNA of a cell.

3. The construct of claim 1 wherein the poly C sequence comprises 2 to 5 cytosine nucleobases.

4. The construct of claim 1, wherein the poly G sequence comprises 2 to 5 guanine nucleobases.

5. The construct of claim 1, wherein the RNA TSO comprises one or more locked nucleic acids (LNAs).

6. The construct of claim 5, wherein the RNA TSO comprises one locked nucleic acid (LNA) at a 3' end of the RNA TSO.

7. The construct of claim 5, wherein 1% to 50% of the nucleotides of the RNA TSO comprise LNAs.

8. The construct of claim 1, wherein the RNA transcript further comprises a reverse transcription priming site.

9. The construct of claim 8, wherein the cDNA strand further comprises a sequence complementary to the reverse transcription priming site.

10. The construct of claim 1, wherein the RNA transcript is an RNA polymerase III-transcribed RNA transcript.

11. The construct of claim 1, wherein the RNA transcript further comprises a target sequence, and wherein the cDNA strand further comprises a reverse complement of the target sequence.

12. The construct of claim 1, wherein the TSO arm sequence is located at a 3' end of the cDNA strand.

13. A construct for performing a rolling circle amplification reaction, the construct comprising:
an RNA transcript from a transfected cell, wherein the RNA transcript comprises a complementary sequence of a padlock arm sequence; and
a cDNA strand, wherein the cDNA strand is hybridized with the RNA transcript and is reverse transcribed from the RNA transcript,
wherein the cDNA strand comprises:
a template switching oligonucleotide (TSO) arm sequence;
a poly C sequence; and a padlock arm sequence, wherein the transfected cell comprises the padlock arm sequence and is produced by inserting the padlock arm sequence into a genome of a cell such that the padlock arm sequence is located in a genome of the transfected cell at a position located less than 100 nucleobases downstream of an RNA polymerase II or RNA polymerase III promoter; and an RNA template switching oligonucleotide (TSO) comprising a poly G sequence, wherein the RNA transcript is transcribed from the genome of the transfected cell wherein the poly G sequence is hybridized to the poly C sequence of the cDNA strand, and wherein a portion of the RNA TSO is hybridized to the TSO arm sequence of the cDNA strand.

14. The construct of claim 13, wherein the cDNA strand further comprises a barcode sequence which encodes for a guide RNA (gRNA) that guides a CRISPR protein to a target site in genomic DNA of a cell.

15. The construct of claim 13, wherein the poly C sequence comprises 2 to 5 cytosine nucleobases or wherein the poly G sequence comprises 2 to 5 guanine nucleobases.

16. The construct of claim 13, wherein the RNA TSO comprises one or more LNAs.

17. The construct of claim 16, wherein the RNA TSO comprises one LNA at a 3' end of the RNA TSO.

18. The construct of claim 16, wherein 1% to 50% of the nucleotides of the RNA TSO comprise LNAs.

19. The construct of claim 13, wherein the RNA transcript further comprises a reverse transcription priming site, and wherein the cDNA strand further comprises a sequence complementary to the reverse transcription priming site.

20. The construct of claim 13, wherein the RNA transcript further comprises a target sequence, and wherein the cDNA strand further comprises a reverse complement of the target sequence.

\* \* \* \* \*